US009365508B2

(12) United States Patent
Lain et al.

(10) Patent No.: US 9,365,508 B2
(45) Date of Patent: *Jun. 14, 2016

(54) AROYL THIOUREA DERIVATIVES

(75) Inventors: Sonia Lain, Stockholm (SE); Nicholas James Westwood, Dundee (GB); David Philip Lane, Fife (GB)

(73) Assignees: University Court of the University of St Andrews (GB); University Court of the University of Dundee (GB)

( * ) Notice: Subject to any disclaimer, the term of this patent is extended or adjusted under 35 U.S.C. 154(b) by 244 days.

This patent is subject to a terminal disclaimer.

(21) Appl. No.: 13/377,145

(22) PCT Filed: Jun. 9, 2010

(86) PCT No.: PCT/GB2010/001136
§ 371 (c)(1),
(2), (4) Date: Feb. 28, 2012

(87) PCT Pub. No.: WO2010/142956
PCT Pub. Date: Dec. 16, 2010

(65) Prior Publication Data
US 2012/0149778 A1    Jun. 14, 2012

(30) Foreign Application Priority Data

Jun. 9, 2009    (GB) .................................... 0909912.8

(51) Int. Cl.
*C07C 335/26*    (2006.01)
*C07C 327/54*    (2006.01)

(52) U.S. Cl.
CPC ............. *C07C 335/26* (2013.01); *C07C 327/54* (2013.01)

(58) Field of Classification Search
None
See application file for complete search history.

(56) References Cited

U.S. PATENT DOCUMENTS

| 2004/0028607 A1 | 2/2004 | Verdin et al. |
| 2004/0138465 A1 | 7/2004 | Spurr |
| 2006/0004085 A1 | 1/2006 | Weber et al. |
| 2009/0163545 A1 | 6/2009 | Goldfarb |

FOREIGN PATENT DOCUMENTS

| EP | 0117320 A1 | 5/1984 |
| EP | 0116728 A1 | 8/1984 |
| EP | 0136745 A | 4/1985 |
| EP | 0193249 A3 | 9/1986 |
| EP | 0475506 A1 | 3/1992 |
| EP | 0545441 A1 | 9/1993 |
| JP | 07285952 A | 10/1995 |
| WO | WO 95/25096 A1 | 9/1995 |
| WO | WO 2004/014885 A1 | 2/2004 |
| WO | WO 2006/083271 A2 | 8/2006 |
| WO | WO 2006/110762 A2 | 10/2006 |
| WO | WO 2008/029096 A2 | 3/2008 |

OTHER PUBLICATIONS

Berkson et al., "Pilot screening programme for small molecule activators of p53", Int. J. Cancer, vol. 115, pp. 701-710 (2005).
Heltwig et al., "Antitumor activity of a small-molecule inhibitor of human silent information regulator 2 enzymes", Cancer Res., vol. 66, No. 8, pp. 4368-4377 (2006).
Hollick et al., "High-throughput screening to identify novel inducers of p53 function", Poster with Abstract, University of St. Andrews and University of Dundee, 2 Pages, (2004).
International Search Report from PCT Patent Application No. PCT/GB2007/003302, 6 pages, mailed on Feb. 20, 2008.
International Preliminary Report on Patentability from PCT Patent Application No. PCT/GB2007/003302, 12 pages, Report completed on Oct. 29, 2008.
Sarkis and Faisal, "Synthesis and spectroscopic properties of some new N,N'-disubstituted thiorueas of potential biological interst", J. Heterocyclic Chem., vol. 22, pp. 137-140 (1985).
Sohn et al., "High-throughput measurement of the Tp53 response to anticancer drugs and random compounds using a stably integrated", Carcinogenesis, vol. 23, No. 6, pp. 949-957 (2002).
STN Chemcats database, Accession No. 2005:4236088 & Scientific Exchange Product List, Compound RN: 496031-65-3, Mar. 14, 2006.
STN Chemcats database, Accession No. 2005:4563741 & Scienctific Exchange Product List Compound RN: 527738-35-8, Mar. 14, 2006.
STN Chemcats database, Accession No. 2006:1409306 & Aurora Screening Library, Compound RN: 477505-90-1, May 10, 2006.
STN Chemcats database, Accession No. 2004:2163350 & ChemStar Product List, Compound RN: 688014-33-7, Apr. 6, 2006.
STN Chemcats database, Accession No. 2004:2163352 & ChemStar Product List, Compound RN: 529481-91-2, Apr. 6, 2006.
STN Chemcats database. Accession No. 2004:2167954 & ChemStar Product List, Compound RN: 689766-20-9, Apr. 6, 2006.
Thakar et al., "Synthesis of thiourea derivatives bearing the benzo [b] thiophene nuclease as potential antimicrobial agents", J. Serb. Chem. Soc., vol. 70, No. 6, pp. 807-815 (2005).
UKIPO search report from GB Patent Application No. GB 0617278.7 mailed on Jan. 23, 2007.
Vassilev et al., "In vivo activation of the p53 pathway by small-molecule antagonists of MDM2", Science, vol. 303, pp. 844-848 (2004).

(Continued)

*Primary Examiner* — Jeffrey S Lundgren
*Assistant Examiner* — Stephanie Springer
(74) *Attorney, Agent, or Firm* — Susan T. Evans; McDermott Will & Emery LLP

(57) ABSTRACT

The invention provides compounds according to formula (I): (wherein X, Y, Z1 R1, R2, R3, Ar and Ar' are as defined herein), and physiologically acceptable salts, solvates, esters or amides thereof, pharmaceutical compositions comprising these compounds and the compounds for use in medicine, for example for the treatment or prophylaxis of diseases involving cell proliferation, such as cancer, and for the treatment or prophylaxis of other diseases.

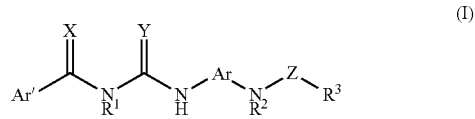

14 Claims, No Drawings

(56) References Cited

OTHER PUBLICATIONS

Written Opinion of the International Searching Authority from PCT Patent Application No. PCT/GB2007/003302, 5 pages, mailed on Feb. 20, 2008.

Bedalov et al., "Identificaticon of a small molecule inhibitor of Sir2p", PNAS, vol. 98, No. 26, pp. 15113-15118 (2001).

Chen et al., "Acylisothiocyanates. IV, p-bromobenzoyl isothiocyanate as a reagent for the identification of amines", Huaxue xuebao, vol. 23, pp. 280-285 (1957), Database CAPLUS [Online] Database accession No. 1958:113331 Abstract Only.

International Search report from related PCT Patent Application No. PCT/GB2010/001136 mailed on Dec. 10, 2010, application now published as WO2010/142956 on Dec. 16, 2010.

Jing et al., "SIRT2 regulates adipocyte differentiation through Fox01 acetylation/deacetylation", Cell Metabolism, vol. 6, pp. 105-114 (2007).

Lain et al., "Discovery, in vivo activity, and mechanism of action of a small-molecule p53 activator", Cancer Cell, vol. 13, No. 5, pp. 454-463 (2008), Database CAPLUS [Online] Database accession No. 2008:593600.

Muravyeva et al., "Synthesis in the series of aromatic derivatives of thiourea", J. Gen. Chem. USSR, vol. 26, pp. 1021-1025 (1956).

Outeiro et al., "Sirtuin 2 inhibitors rescue α-synuclein-mediated toxicity in models of Parkinson's disease", Sciencexpress, pp. 1-8, Jun. 21, 2007.

Picard et al., "Sirt1 promotes fat mobilization in white adipocytes by repressing PPAR-γ", Nature, vol. 429, pp. 771-777 (2004).

Rajappa et al., "Isothiocyanate transposition through a retro-ene reaction: pyrolysis of acylthioureas" J. Chem. Soc., vol. 1, No. 8, pp. 2001-2004 (1979).

Tisler, "p-Chlorobenzoylisothiocyanatals reagens zur charakterislerung von primaren und sekundaren aminen", Fresenius Zeitschrift Fur Anylytische Chemie, vol. 1 pp. 272-275 (1959) German Language Only.

Wang and Tong, "SIRT2 suppresses adipocyte differentiation by deacetylating FOXO1 and enhancing FOXO1's repressive interaction with PPARγ", Mol. Biol. Cell. vol. 20, pp. 801-808 (2009).

AROYL THIOUREA DERIVATIVES

This application is a U.S. National Stage of International Patent Application No. PCT/GB2010/001136, filed Jun. 9, 2010, which claims the benefit of priority to GB Application No. 0909912.8, filed Jun. 9, 2009, each of which is hereby incorporated by reference in its entirety.

INTRODUCTION

The present invention relates to compounds that have been found to activate the p53 tumour suppression protein, including compounds that inhibit the enzymatic activity of SirT1 and SirT2. These compounds thus find use, for example, in the treatment of hyperproliferative diseases such as cancer, metabolic diseases such as diabetes and obesity and neurodegenerative diseases such as Parkinson's and Huntington's diseases.

BACKGROUND OF THE INVENTION

The central role that p53 plays in preventing tumour development is clear although ongoing research continues to dissect the details of how exactly this is achieved. Furthermore, a role for p53 in development, longevity and overall fitness of an organism is starting to emerge (Vousden K H, Lane D P, Nat. Rev. Mol. Cell Biol., 2007 8 (4):275-83). p53 acts as a transcriptional regulator, inducing the expression of a range of anti-proliferative target genes. More than 50% of adult human tumours are characterised by inactivating mutations or deletions of the p53 gene. Other tumour types in which p53 is wild-type frequently have alterations in the mechanisms that control p53 activation. It is widely accepted that activation of the p53 tumour suppressor protein through the use of non-genotoxic compounds may prove therapeutically important.

One class of non-genotoxic p53 activators is known as the tenovins and exemplary compounds of this class are disclosed in WO 2008/029096 and by Lain, S. et al. (Cancer Cell, 2008, 13, 1-10). Tenovins function through inhibition of a group of NAD+-dependent protein deacetylases known as the sirtuins (HDAC class III) (Lain, S. et al. infra)). To date, one sirtuin family member SIRT1 is known to regulate p53 activity by deacetylating p53 at Lys382 (Vaziri H, Dessain S K. N g Eaton E. Imai S I. Frye R A. Pandita T K. Guarente L. Weinberg R A, Cell, 2001 107 (2): 149-59; and Luo J. Nikolaev A Y. Imai S. Chen D. Su F. Shiloh A. Guarentre L. Gue W., Cell, 2001 107 (2):137-48). Partly due to its ability to decrease p53 function, inhibiting SIRT1 is believed to represent an important target for cancer treatment (Lain, S. et al. (infra), Heltweg, B. et al. Cancer Res., 2006 66 (8), 4368-4377 and US 2005/0079995).

Additionally, inhibition of isoforms of SIRT1, particularly SIRT2, as well as SIRT1, are thought to represent an important target for p53 activation and thus cancer therapy (Smith et al., TRENDS in Cell Biology, 2002, 12(9), 404-406.

SIRT2, another of the sirtuins, is comparatively little studied vis-à-vis SIRT1 although, significantly, its inhibition has been linked with treatment for Parkinson's disease and other neurodegenerative disorders such as Huntington's disease (Outeiro T F, Kontopoulos E, Altmann S M, Kufareva I, Strathearn K E, Amore A M, Volk C B, Maxwell M M, Rochet J C, McLean P J, Young A B, Abagyan R, Feany M B, Hyman B T, Kazantsev A G. Sirtuin 2 inhibitors rescue alpha-synuclein-mediated toxicity in models of Parkinson's disease. Science. 2007 Jul. 27; 317(5837):516-9; Luthi-Carter R, Taylor D M, Pallos J, Lambert E, Amore A, Parker A, Moffitt H, Smith D L, Runne H, Gokce O, Kuhn A, Xiang Z, Maxwell M, Reeves S A, Bates G P, Neri C, Thompson L M, Marsh J L, Kazantsev A G. SIRT2 inhibition achieves neuroprotection by decreasing sterol biosynthesis. Proc Natl Acad Sci USA. 2010 Apr. 27; 107(17):7927-32. Epub 2010 Apr. 8). Moreover, Yun-Hye, J. et al. (Biochem. Biophys. Res. Commun., 2008, 368, 690-695) report that SIRT2 interacts with various of the seven isoforms of 14-3-3 proteins, which are highly conserved in nature, including mammals, and expressed in a wide range of tissue types and believed to play critical roles in various cellular mechanisms. Moreover it is also reported in this publication that SIRT2, like SIRT1, deacetylates p53, and down-regulates the transcriptional activity of p53. The inhibitory effect of SIRT2 on p53 is described as enhanced by the β and γ isoforms of 14-3-3. Furthermore, SirT2 inhibition has been suggested to contribute with SirT1 inhibition towards the activation of p53 (Peck B, Chen C Y, Ho K K, Di Fruscia P, Myatt S S, Coombes R C, Fuchter M J, Hsiao C D, Lam E W. SIRT inhibitors induce cell death and p53 acetylation through targeting both SIRT1 and SIRT2. Mol Cancer Ther. 2010 April; 9(4):844-55. Epub 2010 Apr. 6.) Accordingly, in addition to being useful in the treatment of neurodegenerative diseases such as Parkinson's; it is reasonable to postulate that inhibitors of SIRT2, like inhibitors of SIRT1, will allow the development of treatments for diseases associated with abnormalities or deficiencies with the p53 pathway including cancers and other hyperproliferative disorders. Furthermore, SirT2 is clearly involved in the modulation of tubulin acetylation (North B J, Marshall B L, Borra M T, Denu J M, Verdin E. The human Sir2 ortholog, SIRT2, is an NAD+-dependent tubulin deacetylase. Mol. Cell. 2003 February; 11(2):437-44). Because tubulin integrity is essential for cell migration and correct cell cycle progression, compounds that interfere with tubulin function (i.e. tubulin poisons) are well established anticancer agents. Therefore SirT2 inhibitors, through their capacity to increase levels of acetylated tubulin, interfere with tumour cell migration and proliferation.

There remains a need for the development of additional inhibitors, of sirtuins, for example SIRT1 and SIRT2, in particular inhibitors that are selective towards SIRT2 over other sirtuins.

SUMMARY OF THE INVENTION

We have found that compounds structurally distinct from those described in WO2008/029099 have been found to have surprising activity against SIRT2, and that many of these compounds exhibit surprising selectivity towards SIRT2 over SIRT1.

In particular, we have found that compounds structurally related to those described in WO 2008/029096, in which for example additional substituents in the para (tert.butyl) monosubstituted phenyl ring may be present, or wherein the para (tert.butyl) substitutent in the phenyl ring may be omitted (i.e. substituted for hydrogen) or replaced with an alternative substituent.

Viewed from one aspect, therefore, the invention provides a compound according to formula (I):

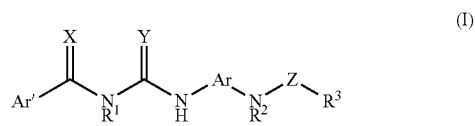

(wherein:

X is O and Y is S or X is S and Y is O;

—Z— is absent or —C(O)—, —C(S)—, —SO$_2$— or —S(O);

Ar is an arylene diradical;

each of —R$^{1'}$—R$^2$ and —R$^3$ is independently —H, -Qalkyl, or -Qaryl, wherein Q is O, NH, S or is absent; and Ar'— is a moiety of the formula (II)

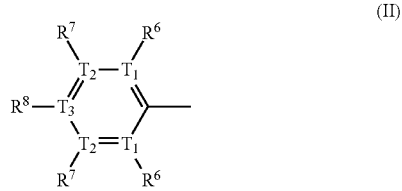

(wherein:

each T$_1$ is independently a nitrogen atom or a carbon atom substituted with R$^6$, which is independently selected from hydrogen, C$_{1-6}$ alkyl, halo, C$_{1-6}$ alkoxy, alkylthio, alkylamino or dialkylamino;

each T$_2$ is independently a nitrogen atom or a carbon atom substituted with R$^7$, which is independently selected from hydrogen, halo, nitro, cyano, carboxy, formyl or C(=O)OR$^4$, C(=S)OR$^4$, C(=O)SR$^4$, C(=S)SR$^4$, C(=O)NH$_2$ or C(=S)NH$_2$ wherein one or both hydrogen atoms may be independently exchanged for R$^4$, C(O)R$^4$, S(O)R$^4$, S(O)$_2$R$^4$ and SO$_2$OR$^4$; and T$_3$ is a nitrogen atom or a carbon atom substituted with R$^8$, which is selected from alkyl, alkoxy, alkylthio, OH, SH, halo, NHC(=O)R$^4$, NHC(=S)R$^4$ or NH$_2$ wherein one or both hydrogen atoms may be independently exchanged for R$^4$, OC(=O)R$^4$, OC(=S)R$^4$, SC(=O)R$^4$, or SC(=S)R$^4$, each R$^4$ is independently selected from the group comprising alkyl or aryl, with the proviso that where R$^8$ is tert butyl, at least one R$^7$ is not hydrogen)), or a physiologically acceptable salt, solvate, ester or amide thereof.

Viewed from a second aspect, the invention provides a compound of the first aspect of this invention, or a physiologically acceptable salt, solvate, ester, or amide thereof, together with a pharmaceutically acceptable carrier.

Viewed from a third aspect, the invention provides a compound of the first aspect of the invention or a physiologically acceptable salt, solvate, ester, or amide thereof, for use in medicine.

Viewed from a fourth aspect, the invention provides a compound of this invention, or a physiologically acceptable salt, solvate, ester, or amide thereof, for the treatment or prophylaxis of a disease involving cell proliferation, in particular cancer.

Viewed from a fifth aspect, the invention provides a compound of this invention, or a physiologically acceptable salt, solvate, ester, or amide thereof, for the treatment or prophylaxis of a disease involving associated with SirT1 or SirT2 expression and/or function, for example diabetes, muscle differentiation, inflammation, aberrant or undesirable immune response, obesity, heart failure, neurodegeneration, HIV infection or malaria, Viewed from a sixth aspect, the invention provides a method of treatment or prophylaxis of a disease involving cell proliferation, in particular cancer, said method comprising administering a therapeutically or prophylactically useful amount of a compound of this invention, or a physiologically acceptable salt, solvate, ester, or amide thereof, to a subject in need thereof.

Viewed from a seventh aspect, the invention provides a method of treatment or prophylaxis of a disease/condition associated with SirT1 or SirT2 expression and/or function said method comprising administering a therapeutically or prophylactically useful amount of a compound of this invention, or a physiologically acceptable salt, solvate, ester, or amide thereof, to a subject in need thereof.

Viewed from a eighth aspect, the invention provides a method of treatment or prophylaxis of a disease/condition selected from the group consisting of diabetes, muscle differentiation, inflammation, aberrant or undesirable immune response, obesity, heart failure, neurodegeneration, HIV infection or malaria, said method comprising administering a therapeutically or prophylactically useful amount of a compound of this invention, or a physiologically acceptable salt, solvate, ester, or amide thereof, to a subject in need thereof.

Viewed from further aspects, the invention provides use of a compound of this invention, or a physiologically acceptable salt, solvate, ester, or amide thereof, in the manufacture of a medicament for use in any method of treatment or prophylaxis defined herein.

Other aspects and embodiments of the invention will be evident from the discussion that follows.

DETAILED DESCRIPTION OF THE INVENTION

The present invention arises from the recognition that the compounds herein possess surprising inhibitory effects against SIRT2 and in particular from the supplementary effect that they show selective inhibition for SIRT2 over SIRT1. The invention is thus surprising, both in that the properties of the compounds, in particular as inhibitors of SIRT2, could not have been predicted from the prior art and also as a result of the structural distinctiveness of the compounds in the light of the prior art, notably WO 2008/029096.

The compounds of formula (I) are now described.

In the compounds of formula (I), X may be oxygen and Y sulfur or vice versa. Typically, X is oxygen and Y is sulfur.

The moiety Z may be absent, or may be a keto (C(O)), thioketo (C(S)), sulfone (SO$_2$) or sulfoxide (S(O)) moiety, in other words —Z— may be, —C(O)—, —C(S)— or —S(O)—. In certain embodiments of the invention, Z is present. In some embodiments in which Z is present it is carbonyl.

Ar is an arylene diradical. Such diradicals are derived from aromatic moieties, formally, by abstraction of two hydrogen atoms.

Arylene diradicals may be monocyclic, for example, phenylene. As known to those skilled in the art, heteroaromatic moieties are a subset of aromatic moieties that comprise one or more heteroatoms, typically O, N or S, in place of one or more carbon atoms and any hydrogen atoms attached thereto. Such exemplary heteroaromatic moieties, for example, include pyridine, furan, pyrrole and pyrimidine.

When the arylene is phenylene for example, its points of connectivity to the remainder of the compound of formula (I) may be through any two of its carbon atoms. Typically, however the —Ar— moiety will be a 1,3- or 1,4-phenylene moiety, typically a 1,4-phenylene moiety.

Alternatively, the aromatic moieties from which the arylene diradicals are derived may be polycyclic, i.e. comprising two or more fused aromatic (including heteroaromatic) rings. Naphthalene and anthracene are examples of polycyclic aromatic moieties, and benzimidazole is an example of a polycyclic heteroaromatic moiety.

Moiety Ar in compounds of formula (I) may thus be a mono-, or poly- (e.g. bi- or tri-cyclic) arylene (including heteroarylene) diradical that may be optionally substituted with one or more substituents selected from halo (e.g. fluoro, chloro, bromo and iodo), alkyl, aryl (including heteroaryl), hydroxy, nitro, amino, alkoxy, alkylthio, carboxy, cyano, thio, formyl, ester, acyl, thioacyl, amido, carbamido and sulfonamido.

In certain embodiments of the invention, Ar in compounds of formula (I) is an optionally substituted monocyclic arylene diradical, in particular a carbocyclic arylene moiety (i.e. one that is not heteroaromatic), more typically still a phenylene group, in particular a 1,4-phenylene group. In certain embodiments of compounds of formula (I) Ar is unsubstituted, e.g. unsubstituted phenylene and in particular an unsubstituted 1,4-phenylene group.

In other embodiments of the invention Ar is a heteroaromatic-containing arylene diradical, typically a monocyclic heteroarylene group (e.g. a pyridylene group) that is optionally substituted. Such Ar groups are advantageous is conferring enhanced solubility upon the compounds, allowing greater ease of, or flexibility in, formulation in certain cases.

Each of —$R^1$, —$R^2$ and —$R^3$ may be independently selected from hydrogen and -Qalkyl or -Qaryl wherein Q may be absent or O, NH, or S. Typically Q (in each of —$R^1$, —$R^2$ and $R^3$) is absent.

By alkyl is meant herein a saturated or unsaturated, but not aromatic, hydrocarbyl moiety, which may be straight-chain, cyclic or branched (typically straight-chain unless the context dictates to the contrary). The alkyl groups described herein may thus have one or more sites of unsaturation, which may be constituted by carbon-carbon double bonds or carbon-carbon triple bonds. Generally, however, the alkyl substituents described herein will be saturated alkyl radicals unless the context dictates to the contrary. Typically alkyl groups will comprise from 1 to 25 carbon atoms, more usually 1 to 10 carbon atoms, more usually still 1 to 6 carbon atoms.

Alkyl groups may be substituted, for example once, twice, or three times, e.g. once, i.e. formally replacing one or more hydrogen atoms of the alkyl group. Examples of such substituents are halo (e.g. fluoro, chloro, bromo and iodo), aryl, heteroaryl, hydroxy, nitro, amino, alkoxy, alkylthio, carboxy, cyano, thio, formyl, ester, acyl, thioacyl, amido, carbamido, sulfonamido and the like. Examples of aryl and heteroaryl substituted alkyl include $CH_2$-aryl (e.g. benzyl) and $CH_2$-heteroaryl.

By carboxy is meant herein the functional group $CO_2H$, which may be in deprotonated form ($CO_2$).

By acyl and thioacyl are meant the functional groups of formulae —C(O)-alkyl or —C(S)-alkyl respectively, where alkyl is as defined hereinbefore.

By amido is meant a functional group comprising the moiety —N(H)C(=O)—;

By carbamido is meant a functional group comprising the moiety —N(H)C(=O)—;

By ester is meant a functional group comprising the moiety —OC(=O)—;

By sulfonamido is meant a functional group comprising the moiety —$SO_2N(H)_2$— in which each hydrogen atom depicted may be replaced (independently in sulfonamido) with alkyl or aryl.

Alkyloxy (synonymous with alkoxy) and alkylthio moieties are of the formulae —O-alkyl and —S-alkyl respectively, where alkyl is as defined hereinbefore.

Alkylamino and dialkylamino moieties are of the formulae —N(H)-alkyl and

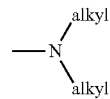

respectively, where alkyl is as defined hereinbefore.

$R^1$ and $R^2$ can each independently be hydrogen alkyl, or aryl, or an alkyl or aryl group connected through Q to the remainder of the compound. Where either or both $R^1$ or $R^2$ is or are a Qalkyl group, this may be of the type specifically described in connection with $R^3$ below. In certain embodiments of the invention of —$R^1$ and —$R^2$ are each, independently, either alkyl or hydrogen, for example unsubstituted alkyl, e.g. unsaturated, unsubstituted alkyl, or hydrogen. In certain embodiments of the invention both $R^1$ and $R^2$ are hydrogen.

—$R^3$ may also be H, -Qalkyl or -Qaryl as described above. In certain embodiments of the invention $R^3$ is other than hydrogen and/or Q is absent. Thus $R^3$ is alkyl or aryl in certain embodiments of the invention. Where $R^3$ is alkyl it may be for example a straight-chain, for example a saturated, straight-chain $C_1$-$C_{20}$ alkyl, e.g. a $C_3$-$C_{10}$ alkyl. Where $R^3$ is other than hydrogen, it may be substituted with one or more, typically one, substituent. The substituents may be independently selected from phenyl, hydroxyl, amino, nitro, alkoxy, alkylthio, formyl, cyano, amido, halo, acyl, $S(O)_2N(R^4)_2$ or $S(O)N(R^4)_2$, $S(O)R^4$ or $SO_2R^4$ wherein $R^4$, is as hereinbefore defined, but typically alkyl or aryl.

Where the $R^3$ moiety is an alkyl group, e.g. a straight-chain alkyl group, such as a straight-chain unsaturated alkyl group, it may in certain embodiments be substituted at its end distal to Z. by this is meant that, in such embodiments, $R^3$ is substituted at the carbon atom furthest away from Z (the terminal carbon atom), or a carbon atom within one to four positions of the terminal carbon atom. In particular embodiments of the invention, $R^3$ is a straight-chain, unsaturated alkyl group substituted at its terminal carbon atom with an amino group.

By amino group is meant herein a group of the formula —$N(R^5)_2$ in which each $R^5$ is independently hydrogen, alkyl or aryl, e.g. an unsaturated, unsubstituted $C_{1-6}$ alkyl such as methyl or ethyl, or in which the two $R^5$s attached to the nitrogen atom N are connected. One example of this is whereby —$R^5$—$R^5$— forms an alkylene diradical, derived formally from an alkane from which two hydrogen atoms have been abstracted, typically from terminal carton atoms, whereby to form a ring together with the nitrogen atom of the amine. As is known the diradical in cyclic amines need not necessarily be alkylene: morpholine (in which —$R^5$—$R^5$— is —$(CH_2)_2O(CH_2)_2$—) is one such example from which a cyclic amino substituent, in particular one with which $R^3$ may be substituted, may be prepared.

References to amino herein are also to be understood as embracing within their ambit quaternised or protonated derivatives of the amines resultant from compounds comprising such amino groups. Examples of the latter may be understood to be salts such as hydrochloride salts.

A particularly structurally distinctive feature of the compounds of the present invention is the substitution pattern on moiety Ar' of formula (II).

Firstly, it will be noted that Ar' is a substituted phenyl or monocyclic heteroaryl. The heteroaryl group may be, for example, pyrdidyl, pyridazine (in which 2 nitrogen atoms are adjacent in an aromatic 6-membered ring); pyrazine (in which 2 nitrogens are 1,4-disposed in a 6-membered aromatic ring); pyrimidine (in which 2 nitrogen atoms are 1,3-disposed in a 6-membered aromatic ring); or 1,3,5-triazine (in which 3 nitrogen atoms are 1,3,5-disposed in a 6-membered aromatic ring).

Typically, however, the symbol $T_3$ and symbols $T_1$ and $T_2$ in formula (II) are each carbon whereby to provide a substituted phenyl moiety as Ar'.

A particularly surprising feature, structurally, of the compounds of formula (I) is that, as discussed hereinabove, Ar' is not 4-tert butyl(phenyl), which in and of itself is a structurally surprising feature in the light of the disclosure in WO2008/029096 and other prior art.

In certain embodiments of the invention wherein $R^8$ is present and is a branched alkyl group, such as isopropyl or tert butyl, for example, at least one $R^7$ is not hydrogen. In other embodiments of the invention, wherein $R^8$ is present and is an alkyl group, at least one $R^7$ is not hydrogen.

Where present, each $R^6$ may be independently selected from hydrogen, $C_{1-6}$ alkyl, halo and $C_{1-6}$ alkoxy or $C_{1-6}$ alkylthio. In certain embodiments of the invention, each $R^6$ where present is hydrogen.

Where present, each $R^7$ is independently selected from hydrogen, halo, nitro, cyano, carboxy, formyl or $C(=O)OR^4$, $C(=S)OR^4$, $C(=O)SR^4$, $C(=S)SR^4$, $C(=O)NH_2$ or $C(=S)NH_2$ wherein one or both hydrogen atoms may be independently exchanged for $R^4$, $C(O)R^4$, $S(O)R^4$, $S(O)_2R^4$ and $SO_2OR^4$.

(Each) $R^4$ is independently alkyl or aryl, typically alkyl, for example unsaturated $C_{1-6}$ alkyl, optionally substituted.

In certain embodiments of the invention at least one $R^7$ is not hydrogen. In other embodiments, both $R^7$s are not hydrogen (and are typically the same). Where one or two $R^7$ substituents are not hydrogen, they are typically $C_{1-6}$ alkyl, halo, $C_{1-6}$ alkoxy, alkylthio, alkylamino or dialkylamino. When halo the $R^7$ substituent(s) may be for example, chloro and bromo, in particular chloro.

Where $T_3$ in formula (II) is not a nitrogen atom, $R^8$ is present and is selected from alkyl, alkoxy, alkylthio, OH, SH, halo, $NHC(=O)R^4$, $NHC(=S)R^4$ or $NH_2$ wherein one or both hydrogen atoms may be independently exchanged for an $R^4$ substituent, $OC(=O)R^4$, $OC(=S)R^4$, $SC(=O)R^4$, or $SC(=S)R^4$, wherein each $R^4$ is as hereinbefore defined.

In certain embodiments of the invention $R^8$ is present and is selected from alkyl, alkoxy, alkylthio or amino. In certain embodiments of the invention $R^8$ is present and is selected from alkyl, alkoxy or amino. In particular, where $R^8$ is alkyl or comprises alkyl—when $R^8$ is alkoxy, alkylthio or alkyl-containing amino—the alkyl present is preferably a saturated alkyl, typically having from 1 to 10 carbon atoms, more typically still 1 to 6 carbon atoms and either substituted only once or not at all. Where $R^8$ is amino this may be therefore as hereinbefore defined although $R^5$ is typically saturated $C_{1-10}$ alkyl, for example methyl or ethyl. In these embodiments of the invention, the alkyl group may advantageously be a straight-chain alkyl group, for example n-propyl, n-pentyl, or n-butyl.

The compounds of the present invention may be used for the treatment and/or prophylaxis of conditions and diseases involving abnormal cell death associated with abnormalities with the p53 protein, its function and/or the p53 pathway.

In particular, diseases involving abnormal proliferation of cells are treatable with the compounds recited herein. Examples of such diseases include cancers, hyperproliferative disorders (including warts, psoriasis, inflammatory bowel disease), rheumatoid/autoimmune conditions, sickle cell anemia and thalasemias.

In addition, the compounds of the present invention are effective at inhibiting sirtuin activity and/or function, in particular of SIRT1 and/or SIRT2. Thus compounds of the present invention may be of use in the treatment or prophylaxis of diseases/conditions associated with expression or functioning of sirtuins in particular SIRT1 and SIRT2, such as cancer, diabetes muscle differentiation, heart failure, neurodegenerative disorders such as Parkinson's disease, aging, HIV infection and malaria.

SIRT1 and related proteins, including other members of the SIRT2 family of enzymes, have been identified as being a target in a great many diseases/conditions, including cancer, ageing, diabetes, muscle differentiation, heart failure, neurodegeneration, HIV infection and malaria (see for example, Bordone L, Guarente L., *Cancer Res.* 2006 Apr. 15; 66(8): 4368-77; Heltweg et al. *Trends Pharmacol Sci.* 2005 February; 26(2):94-103; Pagans et al.; *PLoS Biology* 2005 Vol. 3, No. 2, e41; Deitsch K W, Cell. 2005 Apr. 8; 121(1):1-2; Freitas-Junior L H et al., Cell. 2005 Apr. 8; 121(1):25-36, Nayagam V M, *J. Biomol. Screen.* 2006 Nov. 12). Also, inhibition of SIRT1 as well as inhibition of SIRT2 has been shown to promote adipogenesis (see F Picard et al, *Nature,* 429, 2004, 771-776; F Wang and Q Tong, *Molecular Biology of the Cell,* 20, 2009, 801-808; and E Jing et al., *Cell Metabolism,* 6, 2007, 105-114), meaning that inhibitors of SIRT1 and SIRT2, e.g. SIRT2, may impact upon metabolic disorders, including diabetes and obesity. Accordingly, the compounds of the present invention may find utility in treating/preventing any of these diseases/conditions.

As described hereinbefore, inhibition of SIRT2, in addition to allowing the treatment or prophylaxis of neurodegenerative diseases including Parkinson's disease, and also Huntington's disease, also allows treatment or prophylaxis of diseases involving abnormal proliferation of cells. Examples of such diseases include cancers, hyperproliferative disorders (including warts, psoriasis, inflammatory bowel disease), rheumatoid/autoimmune conditions, sickle cell anemia, thalasemias and the like. Cancers include the cancers described hereinbefore. Thus the compounds of the present invention, particularly of formula (I), are useful in the treatment of prophylaxis of such conditions. Compounds of formula (II) are also useful in the treatment or prophylaxis of diseases including cancer, inflammation, immune response, obesity, ageing, diabetes, muscle differentiation, heart failure, neurodegeneration, HIV infection and malaria.

In certain embodiments of the invention, therefore the compounds are used for the treatment or prophylaxis of cancer.

Examples of cancers which may be treated include, but are not limited to, a carcinoma, for example a carcinoma of the bladder, breast, colon (e.g. colorectal carcinomas such as colon adenocarcinoma and colon adenoma), kidney, epidermal, liver, lung, for example adenocarcinoma, small cell lung cancer and non-small cell lung carcinomas, oesophagus, gall bladder, ovary, pancreas e.g. exocrine pancreatic carcinoma, stomach, cervix, thyroid, prostate, or skin, for example squamous cell carcinoma; a hematopoietic tumour of lymphoid lineage, for example leukaemia, acute lymphocytic leukaemia, B-cell lymphoma, T-cell lymphoma, Hodgkin's lymphoma, non-Hodgkin's lymphoma, hairy cell lymphoma, or Burkett's lymphoma; a hematopoietic tumour of myeloid lineage, for example acute and chronic myelogenous leukaemia's, myelodysplastic syndrome, or promyelocytic leukaemia; thyroid follicular cancer; a tumour of mesenchymal origin, for example fibrosarcoma or habdomyosarcoma; a tumour of the central or peripheral nervous system, for example astrocytoma, neuroblastoma, glioma or schwannoma; melanoma; seminoma; teratocarcinoma; osteosarcoma; xenoderoma pigmentoum; keratoctanthoma; thyroid follicular cancer; or Kaposi's sarcoma.

Other therapeutic agents (e.g. antineoplastic agents) may be administered together (whether concurrently or at different time intervals) with the compounds of the formula (I). Examples of such other therapeutic agents include but are not limited to topoisomerase inhibitors, alkylating agents, antimetabolites, DNA binders and microtubule inhibitors (tubulin target agents), such as cisplatin, cyclophosphamide, doxorubicin, etoposide, irinotecan, fludarabine, 5FU, taxanes or mitomycin C. Other therapeutic agents will be evident to those skilled in the art. For the case of active compounds combined with other therapies the two or more treatments may be given in individually varying dose schedules and via different routes.

The combination of the agents listed above with a compound of the present invention would be at the discretion of the physician who would select dosages using his common general knowledge and dosing regimens known to a skilled practitioner.

Where a compound of the invention is administered in combination therapy with one, two, three, four or more, preferably one or two, preferably one other therapeutic agents, the compounds can be administered simultaneously or sequentially. When administered sequentially, they can be administered at closely spaced intervals (for example over a period of 5-10 minutes) or at longer intervals (for example 1, 2, 3, 4 or more hours apart, or even longer period apart where required), the precise dosage regimen being commensurate with the properties of the therapeutic agent(s).

The compounds of the invention may also be administered in conjunction with non-chemotherapeutic treatments such as radiotherapy, photodynamic therapy, gene therapy; surgery and controlled diets.

The subject is typically an animal, e.g. a mammal, especially a human.

By a therapeutically or prophylactically effective amount is meant one capable of achieving the desired response, and will be adjudged, typically, by a medical practitioner. The amount required will depend upon one or more of at least the active compound(s) concerned, the patient, the condition it is desired to treat or prevent and the formulation of order of from 1 µg to 1 g of compound per kg of body weight of the patient being treated.

Different dosing regiments may likewise be administered, again typically at the discretion of the medical practitioner. As alluded to hereinafter the low toxicity of the compounds of the invention, allow for at least daily administration although regimes where the compound(s) is (or are) administered more infrequently, e.g. every other day, weekly or fortnightly, for example, are also embraced by the present invention.

By treatment is meant herein at least an amelioration of a condition suffered by a patient; the treatment need not be curative (i.e. resulting in obviation of the condition). Analogously references herein to prevention or prophylaxis herein do not indicate or require complete prevention of a condition; its manifestation may instead be reduced or delayed via prophylaxis or prevention according to the present invention.

For use according to the present invention, the compounds or a physiologically acceptable salt, solvate, ester or amide thereof described herein may be presented as a pharmaceutical formulation, comprising the compound or physiologically acceptable salt, ester or other physiologically functional derivative thereof, together with one or more pharmaceutically acceptable carriers therefor and optionally other therapeutic and/or prophylactic ingredients. Any carrier(s) are acceptable in the sense of being compatible with the other ingredients of the formulation and not deleterious to the recipient thereof.

Examples of physiologically acceptable salts of the compounds according to the invention include acid addition salts formed with organic carboxylic acids such as acetic, lactic, tartaric, maleic, citric, pyruvic, oxalic, fumaric, oxaloacetic, isethionic, lactobionic and succinic acids; organic sulfonic acids such as methanesulfonic, ethanesulfonic, benzenesulfonic and p-toluenesulfonic acids and inorganic acids such as hydrochloric, sulfuric, phosphoric and sulfamic acids.

The determination of physiologically acceptable esters or amides, particularly esters is well within the skills of those skilled in the art.

It may be convenient or desirable to prepare, purify, and/or handle a corresponding solvate of the compounds described herein, which may be used in the any one of the uses/methods described. The term solvate is used herein to refer to a complex of solute, such as a compound or salt of the compound, and a solvent. If the solvent is water, the solvate may be termed a hydrate, for example a mono-hydrate, di-hydrate, tri-hydrate etc, depending on the number of water molecules present per molecule of substrate.

It will be appreciated that the compounds of the present invention may exist in various stereoisomeric forms and the compounds of the present invention as hereinbefore defined include all stereoisomeric forms and mixtures thereof, including enantiomers and racemic mixtures. The present invention includes within its scope the use of any such stereoisomeric form or mixture of stereoisomers, including the individual enantiomers of the compounds of formulae (I) or (II) as well as wholly or partially racemic mixtures of such enantiomers.

The compounds of the present invention may be prepared using reagents and techniques readily available in the art and/or exemplary methods as described hereinafter. Appropriate methodology is described in WO2008/029096 and by Lain et al. (infra), and the contents of each being hereby incorporated by reference in their entirety.

Pharmaceutical formulations include those suitable for oral, topical (including dermal, buccal and sublingual), rectal or parenteral (including subcutaneous, intradermal, intramuscular and intravenous), nasal and pulmonary administration e.g., by inhalation. The formulation may, where appropriate, be conveniently presented in discrete dosage units and may be prepared by any of the methods well known in the art of pharmacy. Methods typically include the step of bringing into association an active compound with liquid carriers or finely divided solid carriers or both and then, if necessary, shaping the product into the desired formulation.

Pharmaceutical formulations suitable for oral administration wherein the carrier is a solid are most preferably presented as unit dose formulations such as boluses, capsules or tablets each containing a predetermined amount of active compound. A tablet may be made by compression or moulding, optionally with one or more accessory ingredients. Compressed tablets may be prepared by compressing in a suitable machine an active compound in a free-flowing form such as a powder or granules optionally mixed with a binder, lubricant, inert diluent, lubricating agent, surface-active agent or dispersing agent. Moulded tablets may be made by moulding an active compound with an inert liquid diluent. Tablets may be optionally coated and, if uncoated, may optionally be scored. Capsules may be prepared by filling an active compound, either alone or in admixture with one or more accessory ingredients, into the capsule shells and then sealing them in the usual manner. Cachets are analogous to capsules wherein an active compound together with any accessory ingredient(s) is sealed in a rice paper envelope. An active compound may also be formulated as dispersible granules, which may for example be suspended in water before administration, or sprinkled on food. The granules may be packaged, e.g., in a sachet. Formulations suitable for oral administration wherein the carrier is a liquid may be presented as a solution or a suspension in an aqueous or non-aqueous liquid, or as an oil-in-water liquid emulsion.

Formulations for oral administration include controlled release dosage forms, e.g., tablets wherein an active compound is formulated in an appropriate release-controlling matrix, or is coated with a suitable release-controlling film. Such formulations may be particularly convenient for prophylactic use.

Pharmaceutical formulations suitable for rectal administration wherein the carrier is a solid are most preferably presented as unit dose suppositories. Suitable carriers include cocoa butter and other materials commonly used in the art. The suppositories may be conveniently formed by admixture of an active compound with the softened or melted carrier(s) followed by chilling and shaping in moulds.

Pharmaceutical formulations suitable for parenteral administration include sterile solutions or suspensions of an active compound in aqueous or oleaginous vehicles.

Injectable preparations may be adapted for bolus injection or continuous infusion. Such preparations are conveniently presented in unit dose or multi-dose containers which are sealed after introduction of the formulation until required for use. Alternatively, an active compound may be in powder form which is constituted with a suitable vehicle, such as sterile, pyrogen-free water, before use.

An active compound may also be formulated as long-acting depot preparations, which may be administered by intramuscular injection or by implantation, e.g., subcutaneously or intramuscularly. Depot preparations may include, for example, suitable polymeric or hydrophobic materials, or ion-exchange resins. Such long-acting formulations are particularly convenient for prophylactic use.

Formulations suitable for pulmonary administration via the buccal cavity are presented such that particles containing an active compound and desirably having a diameter in the range of 0.5 to 7 microns are delivered in the bronchial tree of the recipient.

As one possibility such formulations are in the form of finely comminuted powders which may conveniently be presented either in a pierceable capsule, suitably of, for example, gelatin, for use in an inhalation device, or alternatively as a self-propelling formulation comprising an active compound, a suitable liquid or gaseous propellant and optionally other ingredients such as a surfactant and/or a solid diluent. Suitable liquid propellants include propane and the chlorofluorocarbons, and suitable gaseous propellants include carbon dioxide. Self-propelling formulations may also be employed wherein an active compound is dispensed in the form of droplets of solution or suspension.

Such self-propelling formulations are analogous to those known in the art and may be prepared by established procedures. Suitably they are presented in a container provided with either a manually-operable or automatically functioning valve having the desired spray characteristics; advantageously the valve is of a metered type delivering a fixed volume, for example, 25 to 100 microliters, upon each operation thereof.

As a further possibility an active compound may be in the form of a solution or suspension for use in an atomizer or nebuliser whereby an accelerated airstream or ultrasonic agitation is employed to produce a fine droplet mist for inhalation.

Formulations suitable for nasal administration include preparations generally similar to those described above for pulmonary administration. When dispensed such formulations should desirably have a particle diameter in the range 10 to 200 microns to enable retention in the nasal cavity; this may be achieved by, as appropriate, use of a powder of a suitable particle size or choice of an appropriate valve. Other suitable formulations include coarse powders having a particle diameter in the range 20 to 500 microns, for administration by rapid inhalation through the nasal passage from a container held close up to the nose, and nasal drops comprising 0.2 to 5% w/v of an active compound in aqueous or oily solution or suspension.

It should be understood that in addition to the aforementioned carrier ingredients the pharmaceutical formulations described above may include, an appropriate one or more additional carrier ingredients such as diluents, buffers, flavouring agents, binders, surface active agents, thickeners, lubricants, preservatives (including anti-oxidants) and the like, and substances included for the purpose of rendering the formulation isotonic with the blood of the intended recipient.

Pharmaceutically acceptable carriers are well known to those skilled in the art and include, but are not limited to, 0.1 M and preferably 0.05 M phosphate buffer or 0.8% saline. Additionally, pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Preservatives and other additives may also be present, such as, for example, antimicrobials, antioxidants, chelating agents, inert gases and the like.

Formulations suitable for topical formulation may be provided for example as gels, creams or ointments. Such preparations may be applied e.g. to a wound or ulcer either directly spread upon the surface of the wound or ulcer or carried on a suitable support such as a bandage, gauze, mesh or the like which may be applied to and over the area to be treated.

Liquid or powder formulations may also be provided which can be sprayed or sprinkled directly onto the site to be treated, e.g. a wound or ulcer. Alternatively, a carrier such as a bandage, gauze, mesh or the like can be sprayed or sprinkle with the formulation and then applied to the site to be treated.

Therapeutic formulations for veterinary use may conveniently be in either powder or liquid concentrate form. In accordance with standard veterinary formulation practice, conventional water soluble excipients, such as lactose or sucrose, may be incorporated in the powders to improve their physical properties. Thus particularly suitable powders of this invention comprise 50 to 100% w/w and preferably 60 to 80% w/w of the active ingredient(s) and 0 to 50% w/w and preferably 20 to 40% w/w of conventional veterinary excipients. These powders may either be added to animal feedstuffs, for example by way of an intermediate premix, or diluted in animal drinking water.

Liquid concentrates of this invention suitably contain the compound or a derivative or salt thereof and may optionally include a veterinarily acceptable water-miscible solvent, for example polyethylene glycol, propylene glycol, glycerol, glycerol formal or such a solvent mixed with up to 30% v/v of ethanol. The liquid concentrates may be administered to the drinking water of animals.

The invention is now described by the following non-limiting examples:

General Procedure A

The appropriate benzoyl chloride (0.85 mmol) was added to a parallel reactor tube or flask and stirred in acetone (3 mL) under an Ar atmosphere. Sodium thiocyanate (69 mg, 0.85 mmol) was added to each tube or flask and the resulting suspension stirred at room temperature for 16 h. To each reaction tube was added a solution of 5-dimethylamino-pentanoic acid (4-amino-phenyl)-amide (4, prepared as described below) (0.425 mmol) in acetone (2 mL) and the mixtures stirred for at least 4 h. Each reaction was then diluted with dichloromethane (2 mL) and filtered through a short bed of celite. The solvent was then removed from each reaction using the blow down apparatus supplied with the parallel reactor kit. Each reaction was then purified by passing the crude mixture down a short silica column eluting with methanol/dichloromethane (using a gradient of 0, 5, 10, 20%) to give the desired free bases of the compounds described below. The hydrochloride salt of each compound was prepared by dissolving the amine in acetone (1-2 mL) and adding 2 M hydrochloride in diethyl ether (200 µL). The salts were obtained by filtration or decantation of solvent where appropriate.

General Procedure B

The appropriate benzoic acid (500 mg) was stirred in dichloromethane (10 mL) under an Ar atmosphere and thionyl chloride (1.5 equivalents) added followed by several drops of dry dimethylformamide. The mixture was stirred at room temperature for 16 h. Each reaction was concentrated in vacuo and the resulting acid chlorides were used without further purification.

Preparation of 5-dimethylamino-pentanoic acid (4-amino-phenyl)-amide (4)

(4-Amino-phenyl)-carbamic acid benzyl ester (1)

1,4-Phenylenediamine (10 g, 0.093 mol) was stirred rapidly in dichloromethane (800 mL) with diisopropylethylamine (16 mL, 0.093 mol) and the solution cooled to 0° C. A solution of benzyl chloroformate (13 mL, 0.093 mol) in dichloromethane (100 mL) was added very slowly via a dropping funnel. The reaction was left to warm to room temperature over 16 h and concentrated in vacuo. The remaining residue was purified by column chromatography on silica eluting with ethyl acetate/petroleum ether (using a gradient from 25% to 80%) to give 1 as a cream solid (15.5 g, 69.6%).
$^1$H NMR (CDCl$_3$, 400 MHz) δ 3.56 (s(br), 2H, NH$_2$), 5.18 (s, 2H, CH$_2$), 6.45 (s(br), 1H, NH), 6.64 (d, 2H, J=8.8 Hz, ArH), 7.15 (d, 2H, J=6.9 Hz, ArH), 7.36 (m, 5H, ArH).

[4-(5-Bromo-pentanoylamino)-phenyl]-carbamic acid benzyl ester (2)

Aniline 1 (12.69 g, 0.052 mol) was stirred in dichloromethane at 0° C. and 5-bromovaleryl chloride (8.9 mL, 0.052 mol) added followed by diisopropylethylamine (9 mL, 0.052 mol). The resulting white suspension was allowed to warm to room temperature and stirred for 3 h. The white solid was collected by filtration and recrystallised from ethyl acetate to give 2 as a white fluffy powder (10.22 g, 50%).
$^1$H NMR (CDCl$_3$, 400 MHz) δ 1.92 (m, 4H, (CH$_2$)$_2$), 2.38 (t, 2H, J=7.3 Hz, CH$_2$), 3.44 (t, 2H, J=6.2 Hz, CH$_2$), 5.19 (s, 2H, CH$_2$), 6.63 (s(br), 1H, NH), 7.09 (s(br), 1H, NH), 7.36 (m, 7H, ArH), 7.45 (d, 2H, J=8.8 Hz, ArH). HRMS calc'd for C$_{19}$H$_{21}$N$_2$O$_3$NaBr 427.0633. found 427.0637.

[4-(5-Dimethylamino-pentanoylamino)-phenyl]carbamic acid benzyl ester (3)

Compound 2 (5.88 g, 0.012 mol) was stirred in dichloromethane (150 mL) with 40% aqueous dimethylamine (10 mL) and water (25 mL) for 24 h. The solution was diluted with dichloromethane (50 mL) and washed with water (1×100 mL), 1 M aqueous sodium hydroxide (1×100 mL), and saturated brine (1×100 mL). The organic phase was dried (MgSO$_4$) and concentrated in vacuo to give 3 as a white solid (3 g, 68%).
$^1$H NMR (CDCl$_3$, 300 MHz) δ 1.50 (apparent quintet, 2H, J=7.3 Hz, CH$_2$), 1.71 (apparent quintet, 2H, J=7.3 Hz, CH$_2$), 2.22 (s, 6H, N(CH$_3$)$_2$), 2.30 (m, 4H, (CH$_2$)$_2$), 5.18 (s, 2H, CH$_2$), 7.09 (s(br), 1H, NH), 7.33 (m, 5H, ArH), 8.18 (s(br), 1H, NH). HRMS calc'd for C$_{21}$H$_{28}$N$_3$O$_3$ 370.2131. found 370.2131.

5-Dimethylamino-pentanoic acid (4-amino-phenyl)-amide (4)

Compound 3 (1.94 g, 0.005 mol) was stirred in 48% w/v hydrobromic acid in acetic acid (11 mL) for 1 h. Diethylether was added till a cream precipitate appeared and the ethereal solution decanted. The resulting white sticky solid was suspended in dichloromethane (100 mL) and 1 M aqueous sodium hydroxide (20 mL). The aqueous layer was extracted with dichloromethane (1×50 mL) and the combined organic layers were washed with saturated brine (1×50 mL), dried (MgSO$_4$) and concentrated in vacuo to give 4 as a pale yellow oil (975 mg, 82%).
$^1$H NMR (CDCl$_3$, 300 MHz) δ 1.54 (apparent quintet, 2H, J=7.2 Hz, CH$_2$), 1.74 (apparent quintet, 2H, J=7.3 Hz, CH$_2$), 2.23 (s, 6H, N(CH$_3$)$_2$), 2.30 (apparent quartet, 4H, J=7.5 Hz, (CH$_2$)$_2$), 6.62 (d, 2H, J=8.7 Hz, ArH), 7.25 (d, 2H, J=8.6 Hz, ArH), 7.68 (s(br), 1H, NH).

5-Dimethylamino-pentanoic acid {4-[3-(2-methyl-benzoyl)-thioureido]-phenyl}-amide hydrochloride (A1)

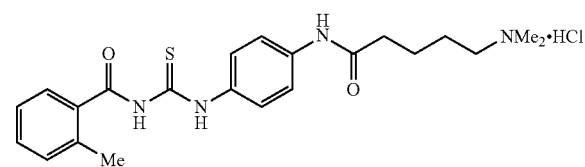

Synthesised according to general procedure A from 2-methyl-benzoyl chloride. White solid, 16.8 mg. $^1$H NMR (DMSO-d$_6$, 400 MHz) δ 1.65 (m, 4H, (CH$_2$)$_2$), 2.39 (m, 2H, CH$_2$), 2.42 (s, 3H, CH$_3$), 2.73 (d, 2H, J=4.9 Hz, N(CH$_3$)$_2$), 3.06 (m, 2H, CH$_2$), 7.31 (d, 2H, J=8.0 Hz, ArH), 7.43 (m, 1H, ArH), 7.50 (d, 1H, J=7.4 Hz, ArH), 7.63 (AA'BB', 4H, J=9.1, 21.5 Hz, ArH), 10.13 (s(br), 1H, NH), 10.20 (s, 1H, NH), 11.69 (s, 1H, NH), 12.46 (s, 1H, NH).

5-Dimethylamino-pentanoic acid {4-[3-(2-chloro-benzoyl)-thioureido]-phenyl}-amide hydrochloride (A2)

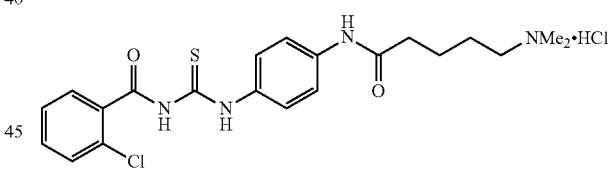

Synthesised according to general procedure A from 2-chloro-benzoyl chloride. Yellow solid, 3.3 mg. $^1$H NMR (DMSO-d$_6$, 300 MHz) δ 1.64 (m, 4H, (CH$_2$)$_2$), 2.39 (t, 2H, J=6.6 Hz, CH$_2$), 2.76 (d, 6H, J=3.7 Hz, N(CH$_3$)$_2$), 3.07 (m, 2H, CH$_2$), 7.56 (m, 8H, ArH), 9.45 (s(br), 1H, NH), 10.10 (s, 1H, NH), 12.00 (s, 1H, NH), 12.27 (s, 1H, NH).

5-Dimethylamino-pentanoic acid {4-[3-(2-methoxy-benzoyl)-thioureido]-phenyl}-amide hydrochloride (A3)

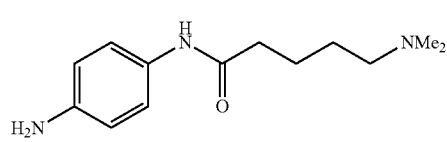 [SMILES: CN(C)CCCCC(=O)Nc1ccc(N)cc1]

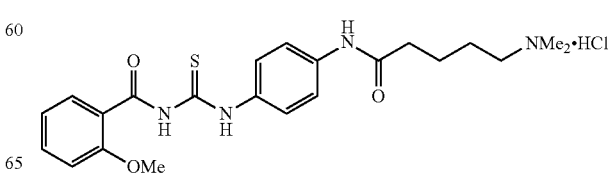

Synthesised according to general procedure A from 2-methoxy-benzoyl chloride. Yellow solid, 8.2 mg. $^1$H NMR (DMSO-$d_6$, 300 MHz) δ 1.63 (m, 4H, (CH$_2$)$_2$), 2.39 (m, 2H, CH$_2$), 2.76 (s, 6H, N(CH$_3$)$_2$), 3.06 (m, 2H, CH$_2$), 4.01 (s, 3H, OCH$_3$), 7.17 (m, 1H, ArH), 7.30 (d, 1H, J=8.5 Hz, ArH), 7.65 (m, 5H, ArH), 7.92 (dd, 1H, J=1.8 Hz, 7.9 Hz, ArH), 9.37 (s(br), 1H, NH), 10.08 (s, 1H, NH), 11.21 (s, 1H, NH), 12.47 (s, 1H, NH).

5-Dimethylamino-pentanoic acid {4-[3-(3-chloro-benzoyl)-thioureido]-phenyl}-amide hydrochloride (A5)

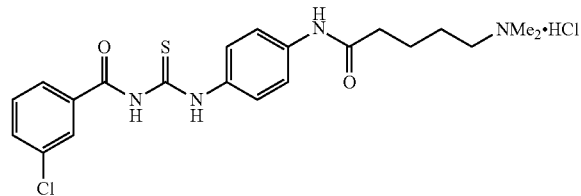

Synthesised according to general procedure A from 3-chloro-benzoyl chloride. Yellow solid, 28 mg. $^1$H NMR (DMSO-$d_6$, 300 MHz) δ 1.64 (m, 4H, (CH$_2$)$_2$), 2.38 (m, 2H, CH$_2$), 2.75 (m, 6H, N(CH$_3$)$_2$), 3.06 (m, 2H, CH$_2$), 7.61 (m, 5H, ArH), 7.73 (d, 1H, J=8.2 Hz, ArH), 8.03 (s, 1H, ArH), 9.65 (s(br), 1H, NH), 10.12 (s, 1H, NH), 11.71 (s, 1H, NH), 12.39 (s, 1H, NH).

5-Dimethylamino-pentanoic acid {4-[3-(3-bromo-benzoyl)-thioureido]-phenyl}-amide hydrochloride (A6)

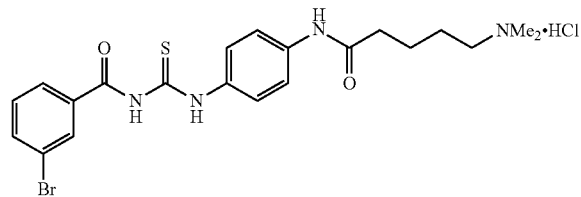

Synthesised according to general procedure A from 3-bromo-benzoyl chloride. Yellow solid, 71 mg. $^1$H NMR (DMSO-$d_6$, 400 MHz) δ 1.62 (m, 4H, (CH$_2$)$_2$), 2.39 (m, 2H, CH$_2$), 2.76 (m, 6H, N(CH$_3$)$_2$), 3.06 (m, 2H, CH$_2$), 7.51 (t, 1H, J=8.1 Hz, ArH), 7.61 (m, 4H, ArH), 7.85 (d, 1H, J=8.5 Hz), 7.94 (d, 1H, J=8.4 Hz), 8.16 (s, 1H, ArH), 9.37 (s(br), 1H, NH) 10.08 (s, 1H, NH), 11.72 (s, 1H, NH), 12.39 (s, 1H, NH).

5-Dimethylamino-pentanoic acid {4-[3-(3-methyl-benzoyl)-thioureido]-phenyl}-amide (B1)

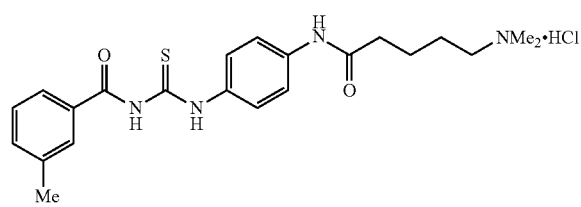

Synthesised according to general procedure A from 3-methyl-benzoyl chloride. Yellow oil, 4.8 mg. $^1$H NMR (DMSO-$d_6$, 400 MHz) δ 1.65 (m, 4H, (CH$_2$)$_2$), 2.39 (m, 2H, CH$_2$), 2.40 (s, 3H, CH$_3$), 2.71 (m, 6H, N(CH$_3$)$_2$), 3.05 (m, 2H, CH$_2$), 7.13 (d, 1H, J=7.7 Hz, ArH), 7.46 (m, 2H, ArH), 7.60 (m, 2H, ArH), 7.66 (d, 1H, J=9.1 Hz, ArH), 7.77 (d, 1H, J=7.3 Hz, ArH), 7.83 (s, 1H, ArH), 10.17 (s(br), 1H, NH), 10.21 (s, 1H, NH), 11.50 (s, 1H, NH), 12.54 (s, 1H, NH).

5-Dimethylamino-pentanoic acid {4-[3-(3-methoxy-benzoyl)-thioureido]-phenyl}-amide hydrochloride (B2)

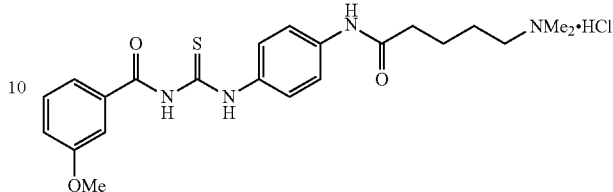

Synthesised according to general procedure A from 3-methoxy-benzoyl chloride. Orange oil, 23.7 mg. $^1$H NMR (DMSO-$d_6$, 400 MHz) δ 1.64 (m, 4H, (CH$_2$)$_2$), 2.38 (m, 2H, CH$_2$), 2.73 (m, 6H, N(CH$_3$)$_2$), 3.03 (m, 2H, CH$_2$), 3.85 (s, 3H, OCH$_3$), 7.22 (dd, 1H, J=2, 7.9 Hz, ArH), 7.45 (t, 1H J=7.9 Hz, ArH), 7.60 (m, 6H, ArH), 9.99 (s(br), 1H, NH), 10.17 (s, 1H, NH), 11.55 (s, 1H, NH), 12.53 (s, 1H, NH).

5-Dimethylamino-pentanoic acid [4-(3-benzoyl-thio-ureido)-phenyl]-amide hydrochloride (B4)

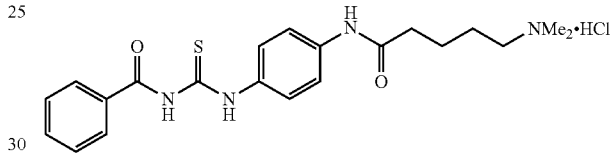

Synthesised according to general procedure A from benzoyl chloride. Yellow solid, 8.8 mg. $^1$H NMR (DMSO-$d_6$, 400 MHz) δ 1.64 (m, 4H, (CH$_2$)$_2$), 2.39 (t, 2H, J=6.9 Hz, CH$_2$), 2.74 (d, 6H, J=4.9 Hz, N(CH$_3$)$_2$), 3.06 (m, 2H, CH$_2$), 7.59 (m, 7H, ArH), 7.97 (d, 2H, J=7.7 Hz, ArH), 9.92 (s(br), 1H, NH), 10.16 (s, 1H, NH), 11.55 (s, 1H, NH), 12.54 (s, 1H, NH).

5-Dimethylamino-pentanoic acid {4-[3-(4-chloro-benzoyl)-thioureido]-phenyl}-amide hydrochloride (318a A1)

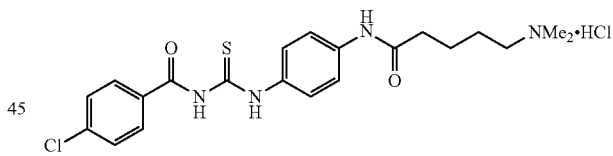

Synthesised according to general procedure A from 4-chloro-benzoyl chloride. Yellow solid, 31 mg. $^1$H NMR (DMSO-$d_6$, 400 MHz) δ 1.75 (m, 4H, (CH$_2$)$_2$), 2.49 (m, 2H, CH$_2$), 2.82 (d, 6H, J=4.7 Hz, N(CH$_3$)$_2$), 3.15 (m, 2H, CH$_2$), 7.71 (m, 6H, ArH), 8.08 (d, 2H, J=7.8 Hz, ArH), 10.34 (s(br), 2H, 2×NH), 11.76 (s, 1H, NH), 12.54 (s, 1H, NH).

5-Dimethylamino-pentanoic acid {4-[3-(4-bromo-benzoyl)-thioureido]-phenyl}-amide hydrochloride (B5)

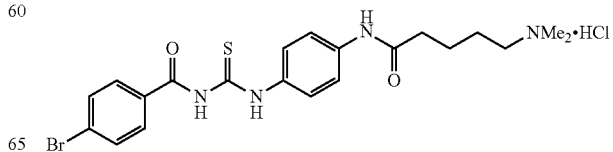

Synthesised according to general procedure A from 4-bromo-benzoyl chloride. Yellow solid, 22.9 mg. $^1$H NMR (DMSO-d$_6$, 400 MHz) δ 1.66 (m, 4H, (CH$_2$)$_2$), 2.39 (m, 2H, CH$_2$), 2.73 (d, 6H, J=4.7 Hz, N(CH$_3$)$_2$), 3.06 (m, 2H, CH$_2$), 7.58 (m, 2H, ArH), 7.66 (m, 2H, ArH), 7.75 (d, 2H, J=8.4 Hz, ArH), 7.91 (m, 2H, ArH).

5-Dimethylamino-pentanoic acid {4-[3-(4-methyl-benzoyl)-thioureido]-phenyl}-amide hydrochloride (318a A2)

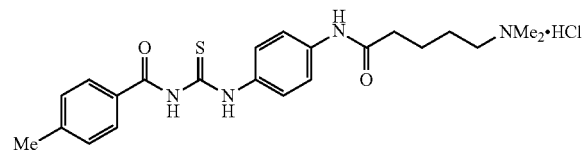

Synthesised according to general procedure A from 4-methyl-benzoyl chloride. Pale brown solid, 7 mg. $^1$H NMR (DMSO-d$_6$, 400 MHz) δ 1.74 (m, 4H, (CH$_2$)$_2$), 2.15 (s, 3H, CH$_3$), 2.42 (m, 2H, CH$_2$), 2.84 (d, 6H, J=4.6 Hz, N(CH$_3$)$_2$), 3.16 (m, 2H, CH$_2$), 7.30 (d, 2H, J=7.8 Hz, ArH), 7.45 (d, 2H, J=8.5 Hz, ArH), 7.75 (d, 2H, J=7.7 Hz, ArH), 8.00 (d, 2H, J=7.8 Hz, ArH), 10.19 (s(br), 1H, NH), 11.44 (s, 1H, NH), 12.70 (s, 1H, NH).

5-Dimethylamino-pentanoic acid {4-[3-(4-methoxy-benzoyl)-thioureido]-phenyl}-amide hydrochloride (318a A3)

Synthesised according to general procedure A from 4-methoxy-benzoyl chloride. Brown solid, 23 mg. $^1$H NMR (DMSO-d$_6$, 400 MHz) δ 1.59 (m, 2H, CH$_2$), 1.72 (m, 2H, CH$_2$), 2.34 (t, 2H, J=8.5 Hz, CH$_2$), 2.79 (d, 6H, J=4.7 Hz, N(CH$_3$)$_2$), 3.08 (m, 2H, CH$_2$), 3.93 (s, 3H, OCH$_3$), 7.16 (d, 4H, J=8.7 Hz, ArH), 7.66 (d, 2H, J=8.7 Hz, ArH), 8.10 (d, 2H, J=8.7 Hz, ArH), 10.19 (s(br), 1H, NH), 11.44 (s, 1H, NH), 12.70 (s, 1H, NH).

5-Dimethylamino-pentanoic acid {4-[(3-(4-trifluoromethyl-benzoyl)-thioureido]-phenyl}-amide hydrochloride (B6)

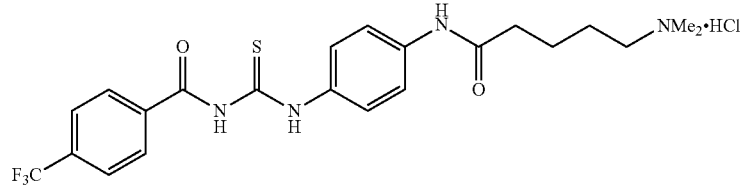

Synthesised according to general procedure A from 4-trifluoromethyl-benzoyl chloride. Cream solid, 3.5 mg. $^1$H NMR (DMSO-d$_6$, 400 MHz) δ 1.66 (m, 4H, (CH$_2$)$_2$), 2.39 (m, 2H, CH$_2$), 2.72 (d, 6H, J=4.5 Hz, N(CH$_3$)$_2$), 3.05 (m, 2H, CH$_2$), 7.64 (m, 4H, ArH), 7.91 (m, 2H, ArH), 8.15 (m, 2H, ArH), 10.41 (s(br), 1H, NH), 10.49 (s, 1H, NH), 11.82 (s, 1H, NH), 12.39 (s, 1H, NH).

5-Dimethylamino-pentanoic acid {4-[3-(4-isopropyl-benzoyl)-thioureido]-phenyl}-amide hydrochloride (331a)

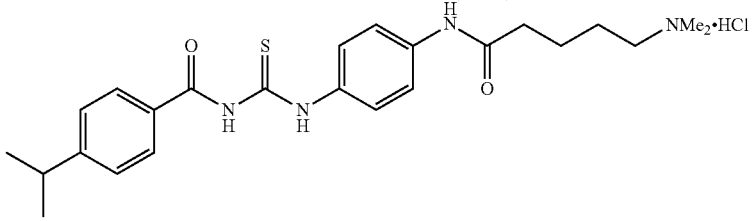

Synthesised according to general procedure A from 4-isopropyl-benzoyl chloride (prepared according to general procedure B from 4-isopropyl-benzoic acid). Yellow oil, 24.7 mg. $^1$H NMR (DMSO-$d_6$, 400 MHz) δ 1.23 (d, 6H, J=6.9 Hz, CH(CH$_3$)$_2$), 1.66 (m, 4H, (CH$_2$)$_2$), 2.37 (m, 2H, CH$_2$), 2.71 (m, 6H, N(CH$_3$)$_2$), 3.02 (m, 1H, CH(CH$_3$)$_2$), 7.42 (d, 2H, J=8.3 Hz, ArH), 7.62 (AA'BB', 4H, J=9.0, 27.4 Hz, ArH), 7.93 (d, 2H, J=8.3 Hz, ArH), 10.16 (s(br), 1H, NH), 10.21 (s, 1H, NH), 11.43 (s, 1H, NH), 12.59 (s, 1H, NH).

5-Dimethylamino-pentanoic acid {4-[3-(4-dimethylamino-benzoyl)-thioureido]-phenyl}-amide hydrochloride (332a)

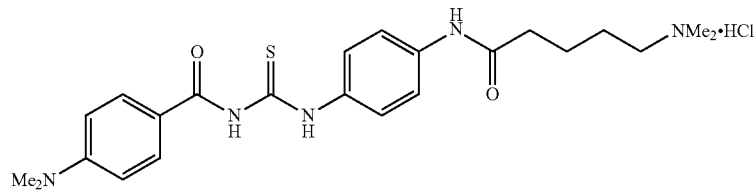

Synthesised according to general procedure A from 4-dimethylamino-benzoyl chloride (prepared according to general procedure B from 4-dimethylamino-benzoic acid). Orange oil, 10 mg. $^1$H NMR (DMSO-$d_6$, 400 MHz) δ 1.64 (m, 4H, (CH$_2$)$_2$), 2.39 (t, 2H, J=6.5 Hz), 2.73 (d, 2H, J=4.9 Hz, CH$_2$N(CH$_3$)$_2$), 3.04 (s, 6H, ArN(CH$_3$)$_2$), 3.04 (m, 2H, CH$_2$), 6.75 (d, 2H, J=9.3 Hz, ArH), (AA'BB', 4H, J=9.1, 24.0 Hz, ArH), 7.93 (d, 2H, J=9.1 Hz, ArH), 10.07 (s(br), 1H, NH), 10.17 (s, 1H, NH), 11.01 (s, 1H, NH), 12.88 (s, 1H, NH).

5-Dimethylamino-pentanoic acid {4-[3-(3,4-dimethyl-benzoyl)-thioureido]-phenyl}-amide hydrochloride (C4)

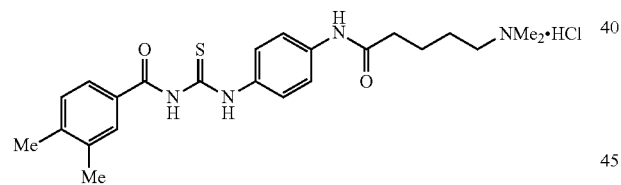

Synthesised according to general procedure A from 3,4-dimethyl-benzoyl chloride. Pale yellow solid, 13.2 mg. $^1$H NMR (DMSO-$d_6$, 300 MHz) δ 1.64 (m, 4H, (CH$_2$)$_2$), 2.30 (s, 6H, 2×CH$_3$), 2.39 (t, 2H, J=6.7 Hz, CH$_2$), 2.74 (s, 6H, N(CH$_3$)$_2$), 3.06 (t, 2H, J=7.1 Hz, CH$_2$), 7.30 (d, 1H, J=8.1 Hz, ArH), 7.62 (AA'BB', 4H, J=9.1, 18.5 Hz, ArH), 7.73 (dd, 1H, J=1.6, 7.7 Hz, ArH), 7.82 (s, 1H, ArH), 9.81 (s(br), 1H, NH), 10.14 (s, 1H, NH), 11.38 (s, 1H, NH), 12.61 (s, 1H, NH).

5-Dimethylamino-pentanoic acid {4-[3-(3-bromo-4-methyl-benzoyl)-thioureido]-phenyl}-amide hydrochloride (330a)

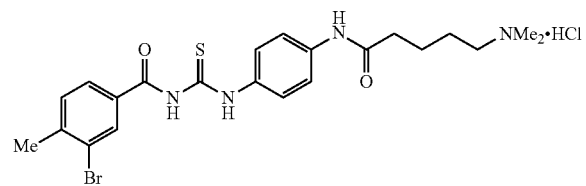

Synthesised according to general procedure A from 3-bromo-4-methyl-benzoyl chloride (prepared according to general procedure B from 3-bromo-4-methyl-benzoic acid). Pale yellow solid, 35 mg. $^1$H NMR (DMSO-$d_6$, 400 MHz) δ 1.66 (m, 4H, (CH$_2$)$_2$), 2.39 (m, 2H, CH$_2$), 2.43 (s, 3H, CH$_3$), 2.74 (s, 6H, N(CH$_3$)$_2$), 3.06 (m, 2H, CH$_2$), 7.53 (d, 1H, J=8.2 Hz, ArH), 7.62 (AA'BB', 4H, J=8.9, 27.2 Hz, ArH), 7.89 (dd, 1H, J=1.5, 8.1 Hz, ArH), 8.21 (d, 1H, J=1.4 Hz, ArH), 9.89 (s(br), 1H, NH), 10.16 (s, 1H, NH), 11.67 (s, 1H, NH), 12.44 (s, 1H, NH).

5-Dimethylamino-pentanoic acid {4-[3-(4-bromo-3-methyl-benzoyl)-thioureido]-phenyl}-amide hydrochloride (C5)

Synthesised according to general procedure A from 4-bromo-3-methyl-benzoyl chloride. Yellow solid, 27.5 mg. $^1$H NMR (DMSO-$d_6$, 300 MHz) δ 1.66 (m, 4H, (CH$_2$)$_2$), 2.39 (t, 2H, J=6.8 Hz, CH$_2$), 2.43 (s, 3H, CH$_3$), 2.75 (d, 6H, J=4.9 Hz, N(CH$_3$)$_2$), 3.06 (m, 2H, CH$_2$), 7.62 (AA'BB', 4H, J=8.9, 29.5 Hz, ArH), 7.62 (m, 2H, ArH), 7.98 (d, 1H, J=1.9 Hz, ArH), 10.02 (s(br), 1H, NH), 10.19 (s, 1H, NH), 11.59 (s, 1H, NH), 12.46 (s, 1H, NH).

5-Dimethylamino-pentanoic acid {4-[3-(4-methoxy-3-trifluoromethyl-benzoyl)-thioureido]-phenyl}-amide hydrochloride (C6)

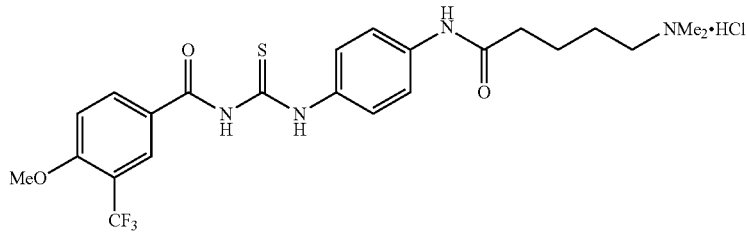

Synthesised according to general procedure A from 4-methoxy-3-trifluoromethyl-benzoyl chloride. Yellow solid, 25.9 mg. $^1$H NMR (DMSO-d$_6$, 300 MHz) δ 1.64 (m, 4H, (CH$_2$)$_2$), 2.39 (t, 2H, J=6.1 Hz, CH$_2$), 2.74 (s, 6H, N(CH$_3$)$_2$), 3.06 (m, 2H, CH$_2$), 4.00 (s, 3H, OCH$_3$), 7.40 (dd, 2H, J=9.3, 12.3 Hz, ArH), 7.63 (m, 3H, ArH), 8.29 (m, 2H, ArH), 9.54 (s(br), 1H, NH), 10.10 (s, 1H, NH), 11.74 (s, 1H, NH), 12.51 (s, 1H, NH).

5-Dimethylamino-pentanoic acid {4-[3-(3,4-dichloro-benzoyl)-thioureido]-phenyl}-amide hydrochloride (311d)

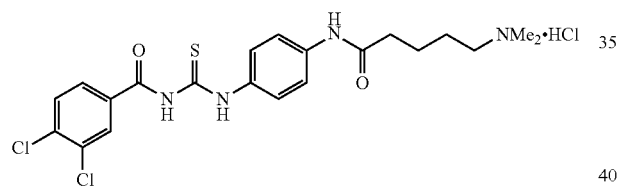

Synthesised according to general procedure A from 3,4-dichloro-benzoyl chloride. Brown solid, 90 mg. $^1$H NMR (DMSO-d$_6$, 300 MHz) δ 1.74 (m, 4H, (CH$_2$)$_2$), 2.48 (m, 2H, CH$_2$), 2.84 (m, 6H, N(CH$_3$)$_2$), 3.16 (m, 2H, CH$_2$), 7.72 (m, 5H, ArH), 7.88 (d, 2H, J=1.93 Hz, ArH), 9.93 (s(br), 1H, NH), 10.26 (s, 1H, NH), 12.11 (s, 1H, NH), 12.29 (s, 1H, NH).

5-Dimethylamino-pentanoic acid {4-[3-(3-chloro-4-methoxy-benzoyl)-thioureido]-phenyl}-amide hydrochloride (350a)

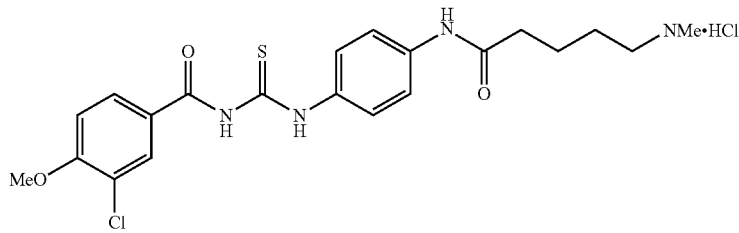

Synthesised according to general procedure A from 3-chloro-4-methoxy-benzoyl chloride. Yellow solid, 27 mg. $^1$H NMR (DMSO-d$_6$, 300 MHz) δ 1.64 (m, 4H, (CH$_2$)$_2$), 2.39 (d, 2H, J=6.9 Hz), 2.74 (d, 6H, J=4.9 Hz, N(CH$_3$)$_2$), 3.06 (m, 2H, CH$_2$), 3.98 (s, 3H, OCH$_3$), 7.30 (d, 1H, J=8.7 Hz, ArH), 7.62 (AA'BB', 4H, J=8.7, 25.4 Hz, ArH), 8.02 (dd, 1H, J=2.0, 8.6 Hz, ArH), 8.13 (d, 1H, J=2.0 Hz), 9.73 (s(br), 1H, NH), 10.14 (s, 1H, NH), 11.53 (s, 1H, NH), 12.52 (s, 1H, NH).

5-Dimethylamino-pentanoic acid {4-[3-(3,4,5-trifluoro-benzoyl)-thioureido]-phenyl}-amide hydrochloride (D1)

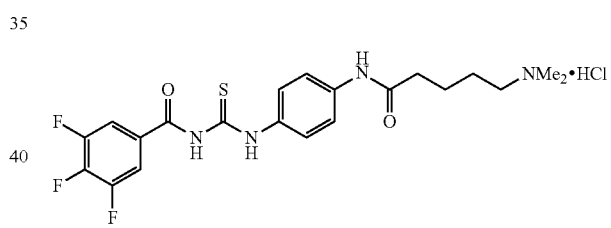

Synthesised according to general procedure A from 3,4,5-trifluoro-benzoyl chloride. Pale yellow solid, 12.3 mg. $^1$H NMR (DMSO-d$_6$, 300 MHz) δ 1.64 (m, 4H, (CH$_2$)$_2$), 2.39 (t, 2H, J=6.6 Hz, CH$_2$), 2.74 (s, 6H, N(CH$_3$)$_2$), 3.06 (m, 2H, CH$_2$), 7.61 (AA'BB', 4H, J=9.0, 24.4 Hz, ArH), 7.99 (dd, 2H, J=6.8, 8.5 Hz, ArH), 9.82 (s(br), 1H, NH), 10.14 (s, 1H, NH), 11.70 (s, 1H, NH), 12.25 (s, 1H, NH).

5-Dimethylamino-pentanoic acid {4-[3-(3,4,5-trimethoxy-benzoyl)-thioureido]-phenyl}-amide hydrochloride (D2)

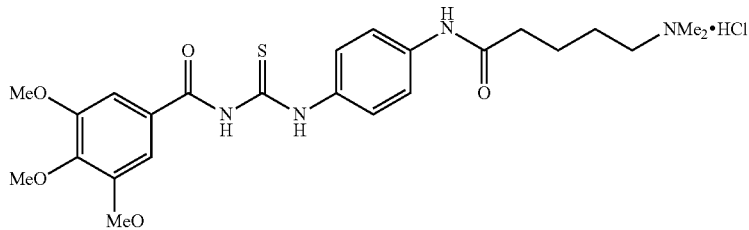

Synthesised according to general procedure A from 3,4,5-trimethoxy-benzoyl chloride. Yellow solid, 36.3 mg. $^1$H NMR (DMSO-$d_6$, 300 MHz) δ 1.65 (m, 4H, (CH$_2$)$_2$), 2.39 (t, 2H, J=6.5 Hz, CH$_2$), 2.75 (d, 6H, J=4.9 Hz, N(CH$_3$)$_2$), 3.06 (m, 2H, CH$_2$), 3.75 (s, 3H, OCH$_3$), 3.88 (s, 6H, 2×OCH$_3$), 7.38 (s, 2H, ArH), 7.62 (AA'BB', 4H, ArH), 9.82 (s(br), 1H, NH), 10.15 (s, 1H, NH), 11.56 (s, 1H, NH), 12.65 (s, 1H, NH).

5-Dimethylamino-pentanoic acid {4-[3-(3,5-dichloro-4-methoxy-benzoyl)-thioureido]-phenyl}-amide hydrochloride (D3)

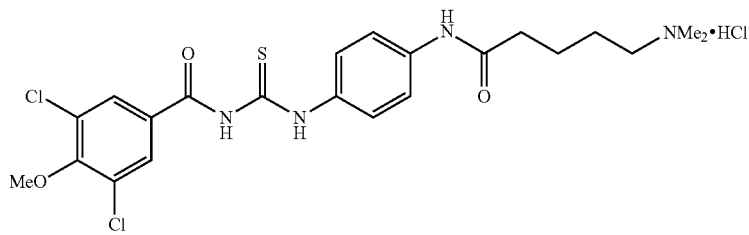

Synthesised according to general procedure A from 3,5-dichloro-4-methoxy-benzoyl chloride. Orange solid, 14.4 mg. $^1$H NMR (DMSO-$d_6$, 300 MHz) δ 1.64 (m, 4H, (CH$_2$)$_2$), 2.39 (t, 2H, J=6.2 Hz, CH$_2$), 2.76 (d, 6H, J=4.8 Hz, N(CH$_3$)$_2$), 3.07 (m, 2H, CH$_2$), 7.61 (AA'BB', 4H, J=8.9, 19.5 Hz, ArH), 8.11 (s, 2H, ArH), 9.39 (s(br), 1H, NH), 10.08 (s, 1H, NH), 11.73 (s, 1H, NH), 12.31 (s, 1H, NH).

5-Dimethylamino-pentanoic acid {4-[3-(4-pentyl-benzoyl)-thioureido]-phenyl}-amide hydrochloride (345a)

Synthesised according to general procedure A from 4-n-pentyl-benzoyl chloride. Yellow solid, 80 mg. $^1$H NMR (DMSO-$d_6$, 300 MHz) δ 0.86 (t, 3H, J=6.8 Hz, CH$_3$), 1.29 (m, 4H, (CH$_2$)$_2$), 1.62 (m, 6H, (CH$_2$)$_3$), 2.39 (t, 3H, J=6.7 Hz, CH$_2$), 2.66 (m, 2H, CH$_2$), 2.73 (m, 6H, N(CH$_3$)$_2$), 3.02 (m, 2H, CH$_2$), 7.36 (d, 2H, J=8.4 Hz, ArH), 7.62 (AA'BB', 4H, J=9.0, 20.1 Hz, ArH), 7.91 (d, 2H, J=8.3 Hz, ArH), 9.98 (s(br), 1H, NH), 10.18 (s, 1H, NH), 11.44 (s, 1H, NH), 12.58 (s, 1H, NH).

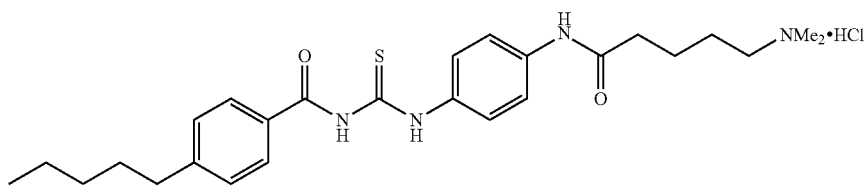

5-Dimethylamino-pentanoic acid {4-[3-(4-butyl-benzoyl)-thioureido]-phenyl}-amide hydrochloride (345b)

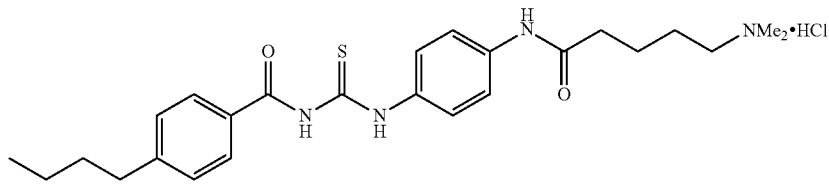

Synthesised according to general procedure A from 4-n-butyl-benzoyl chloride. Yellow oil, 32 mg. $^1$H NMR (DMSO-$d_6$, 300 MHz) δ 0.91 (t, 3H, J=7.3 Hz, $CH_3$), 1.31 (q, 2H, J=7.3 Hz), 1.60 (m, 6H, $(CH_2)_3$), 2.39 (t, 2H, J=6.6 Hz, $CH_2$), 2.67 (m, 2H, $CH_2$), 2.75 (d, 6H, J=4.9 Hz, $N(CH_3)_2$), 3.06 (m, 2H, $CH_2$), 7.36 (d, 2H, J=8.3 Hz, ArH), 7.62 (AA'BB', 4H, J=9 Hz, ArH), 7.91 (d, 2H, J=8.2 Hz, ArH), 9.70 (s(br), 1H, NH), 10.13 (s, 1H, NH), 11.44 (s, 1H, NH), 12.58 (s, 1H, NH).

5-Dimethylamino-pentanoic acid {4-[3-(4-propyl-benzoyl)-thioureido]-phenyl}-amide hydrochloride (345c)

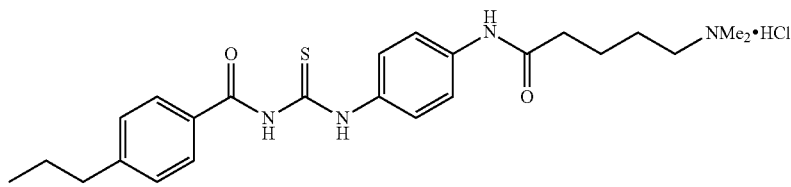

Synthesised according to general procedure A from 4-n-propyl-benzoyl chloride. Orange solid, 95 mg. $^1$H NMR (DMSO-$d_6$, 300 MHz) δ 0.90 (t, 3H, J=7.3 Hz, $CH_3$), 1.64 (m, 6H, $(CH_2)_3$), 2.39 (t, 2H, J=6.5 Hz, $CH_2$), 2.64 (m, 2H, $CH_2$), 2.73 (d, 6H, J=4.9 Hz, $N(CH_3)_2$), 3.05 (m, 2H, $CH_2$), 7.36 (d, 2H, J=8.3 Hz, ArH), 7.62 (AA'BB', 4H, J=9.0, 20.9 Hz, ArH), 7.92 (d, 2H, J=8.2 Hz, ArH), 10.10 (s(br), 1H, NH), 10.20 (s, 1H, NH), 11.40 (s, 1H, NH), 12.58 (s, 1H, NH).

5-Dimethylamino-pentanoic acid {4-[3-(4-ethyl-benzoyl)-thioureido]-phenyl}-amide hydrochloride (345d)

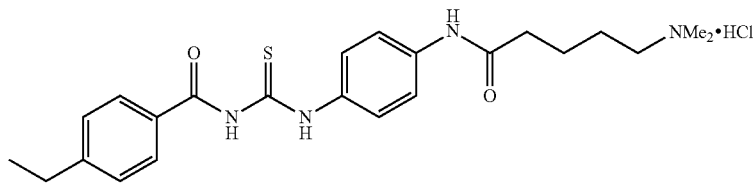

Synthesised according to general procedure A from 4-ethyl-benzoyl chloride. Orange solid, 25 mg. $^1$H NMR (DMSO-$d_6$, 300 MHz) δ 1.21 (t, 3H, J=7.6 Hz, $CH_3$), 1.63 (m, 4H, $(CH_2)_2$), 2.39 (m, 2H, $CH_2$), 2.69 (m, 2H, $CH_2$), 2.73 (d, 6H, J=4.9 Hz, $N(CH_3)_2$), 3.04 (m, 2H, $CH_2$), 7.38 (d, 2H, J=8.3 Hz, ArH), 7.62 (AA'BB', 4H, J=9.1, 28.1 Hz, ArH), 7.93 (d, 2H, J=8.2 Hz, ArH), 10.13 (s(br), 1H, NH), 10.21 (s, 1H, NH), 11.45 (s, 1H, NH), 12.59 (s, 1H, NH).

Preparation of Second Generation Analogues

3-Bromo-4-tert-butyl-benzoic acid 4-tert-butyl benzoic acid (500 mg, 2.8 mmol) was stirred rapidly in acetic acid (11 mL), nitric acid (1.7 mL) and bromine (114 µL, 5.9 mmol). To this was added a solution of silver nitrate (1.01 g, 5.9 mmol) in water (5 mL). A thick yellow precipitate resulted and further acetic acid was added (2 mL) before heating at reflux for 1 h. The hot solution was filtered and water added to the filtrate until a white solid precipitated. The solid was filtered, air dried and recrystallised from acetic acid to give 3-bromo-4-tert-butyl-benzoic acid as a white solid (263 mg, 36%). $^1$H NMR (CDCl$_3$, 300 MHz) δ 1.85 (s, 9H, $(CH_3)_3$), 7.86 (d, 1H, J=8.5 Hz, ArH), 8.26 (dd, 1H, J=2.0, 8.5 Hz, ArH), 8.62 (d, 1H, J=2.0 Hz).

5-Dimethylamino-pentanoic acid {4-[3-(3-bromo-4-tert-butyl-benzoyl)-thioureido]-phenyl}-amide hydrochloride (361a)

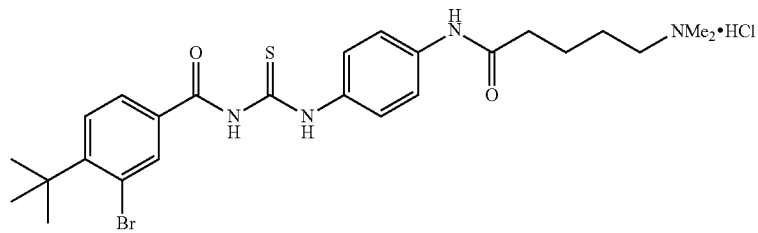

3-Bromo-4-tert-butyl-benzoyl chloride was prepared according to general procedure B from 3-bromo-4-tert-butyl-benzoic acid (500 mg) and used without further purification. 3-Bromo-4-tert-butyl-benzoyl chloride (295 mg, 1.07 mmol) was stirred in acetone (5 mL) and sodium thiocyanate (87 mg, 1.07 mmol) added to give a red-orange suspension which was stirred at room temperature for 16 h. A solution of 5-dimethylamino-pentanoic acid (4-amino-phenyl)-amide (4, prepared as described above) in acetone (5 mL) was added and the yellow suspension stirred for a further 16 h. The reaction mixture was diluted in dichloromethane and filtered to give a crude mixture which was purified by column chromatography eluting with methanol/dichloromethane (0% to 20%) to give 5-dimethylamino-pentanoic acid {4-[3-(3-bromo-4-tert-butyl-benzoyl)-thioureido]-phenyl}-amide as a yellow solid. The hydrochloride salt was prepared by dissolving the amine in a minimal volume of acetone (1-2 mL) and adding 2 M hydrochloric acid in diethyl ether (200 μL). The resulting solid was filtered to give 5-dimethylamino-pentanoic acid {4-[3-(3-bromo-4-tert-butyl-benzoyl)-thioureido]-phenyl}-amide hydrochloride (50 mg) as a yellow solid.

$^1$H NMR (DMSO-$d_6$, 400 MHz) δ 1.61 (s, 9H, (CH$_3$)$_3$), 1.76 (m, 4H, (CH$_2$)$_2$), 2.35 (m, 2H, CH$_2$) 2.83 (d, 6H, J=4.8 Hz, N(CH$_3$)$_2$), 3.17 (m, 2H, CH$_2$), 7.71 (m, 4H, ArH), 8.03 (m, 2H, ArH), 8.32 (d, 1H, J=1.8 Hz, ArH), 10.07 (s(br), 1H, NH), 10.28 (s, 1H, NH), 11.79 (s, 1H, NH), 12.56 (s, 1H, NH).

5-Dimethylamino-pentanoic acid {4-[3-(3-chloro-4-methoxy-benzoyl)-thioureido]-phenyl}-amide hydrochloride (350a)

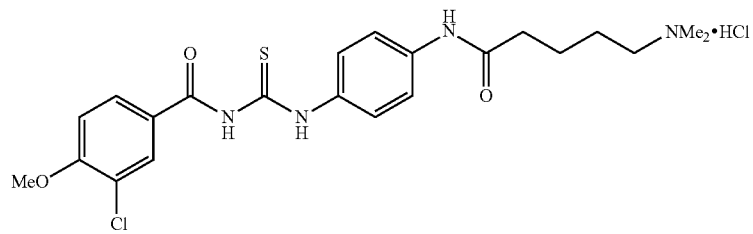

Synthesised according to general procedure A from 3-chloro-4-methoxy-benzoyl chloride (prepared according to general procedure B from 3-chloro-4-methoxy-benzoic acid). Purification by column chromatography eluting with methanol/dichloromethane (0% to 20%) followed by treatment with 2 M hydrochloric acid in diethyl ether gave 350a (27 mg) as a yellow solid. $^1$H NMR (DMSO-$d_6$, 400 MHz) δ 1.64 (m, 4H, (CH$_2$)$_2$), 2.39 (t, 2H, J=6.9 Hz, CH$_2$), 2.79 (d, 6H, J=4.8 Hz, N(CH$_3$)$_2$), 3.06 (m, 2H, CH$_2$), 3.98 (s, 3H, OCH$_3$), 7.30 (d, 1H, J=8.7 Hz, ArH), 7.62 (AA'BB', 4H, J=8.7, 25.4 Hz, ArH), 8.02 (dd, 1H, J=2.0, 8.6 Hz, ArH), 8.13 (d, 1H, J=2.0 Hz, ArH), 9.73 (s(br), 1H, NH), 10.14 (s, 1H, NH), 11.53 (s, 1H, NH), 12.52 (s, 1H, NH). LRMS (M-Cl) Found 533.02/535.01.

5-Dimethylamino-pentanoic acid {4-[3-(3,5-dichloro-benzoyl)-thioureido]-phenyl}-amide hydrochloride (360a)

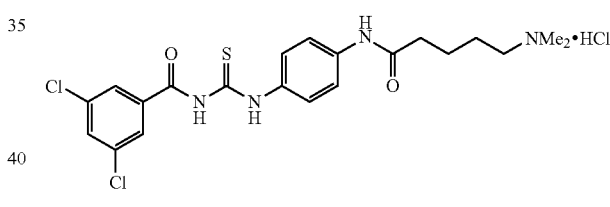

Synthesised according to general procedure A from 3,5-dichlorobenzoyl chloride. Purification by column chromatography eluting with methanol/dichloromethane (0% to 20%) followed by treatment with 2 M hydrochloric acid in diethyl ether gave 360a (93 mg) as a yellow solid. $^1$H NMR (DMSO-$d_6$, 400 MHz) δ 1.73 (m, 4H, (CH$_2$)$_2$), 2.39 (m, 2H, CH$_2$), 2.83 (d, 6H, J=5.0 Hz, N(CH$_3$)$_2$), 3.15 (m, 2H, CH$_2$), 7.70 (AA'BB', 4H, J=8.3, 32.8 Hz, ArH), 8.02 (m, 1H, ArH), 8.06 (d, 1H, J=1.72 Hz, ArH), 10.04 (s(br), 1H, NH), 10.27 (s, 1H, NH), 11.89 (s, 1H, NH), 12.37 (s, 1H, NH).

5-Dimethylamino-pentanoic acid {4-[3-(3,5-di-bromo-4-methoxy-benzoyl)-thioureido]-phenyl}-amide hydrochloride (383a)

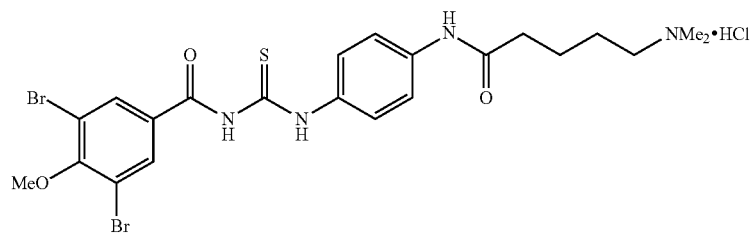

Synthesised according to general procedure A from 3,5-dibromo-4-methoxy-benzoyl chloride. Purification by column chromatography eluting with methanol/dichloromethane (0% to 20%) followed by treatment with 2 M hydrochloric acid in diethyl ether gave 383a (40 mg) as a yellow solid. (DMSO-$d_6$, 400 MHz) δ 1.74 (m, 4H, $(CH_2)_2$), 2.48 (m, 2H $CH_2$), 2.83 (d, 6H, J=4.8 Hz, $N(CH_3)_2$), 3.14 (m, 2H, $CH_2$), 3.96 (s, 3H, $OCH_3$), 7.69 (AA'BB', 4H, J=8.8, 29.0 Hz, ArH), 8.34 (s, 2H, ArH), 9.75 (s(br), 1H, NH), 10.21 (s, 1H, NH), 11.85 (s, 1H, NH), 12.41 (s, 1H, NH).

4-Butoxy-3,5-dichloro-benzoic acid 3,5-Dichloro-4-hydroxy-benzoic (400 mg, 1.93 mmol) was stirred in tetrahydrofuran (5 mL) with 40% aqueous n-tetrabutyl phosphonium hydroxide (3.16 mL, 3.86 mmol) at 0° C. for 5 mins and iodobutane (219 μL, 1.93 mmol) added. The reaction mixture was left to warm to room temperature and stirred for 6 h. The solution was concentrated in vacuo and the remaining residue acidified with concentrated hydrochloric acid to give a white suspension. The mixture was extracted with dichloromethane (3×25 mL) and the combined organic phases washed with saturated brine. The organic layer was dried ($MgSO_4$) and concentrated in vacuo to give a crude mixture which was purified by column chromatography eluting with methanol/dichloromethane (0% to 5%) to give 4-butoxy-3,5-dichloro-benzoic acid (221 mg, 44%) as a white powder. $^1$H NMR ($CDCl_3$, 300 MHz) δ 0.99 (t, 3H, J=7.5 Hz, $CH_3$), 1.56 (sextet, 2H, J=7.5 Hz, $CH_2$), 1.85 (pentet, 2H, J=6.3 Hz, $CH_2$), 4.10 (t, 2H, J=6.3 Hz, $CH_2$), 8.03 (s, 2H, ArH).

5-Dimethylamino-pentanoic acid {4-[3-(4-butoxy-3,5-dichloro-benzoyl)-thioureido]-phenyl}-amide hydrochloride (392a)

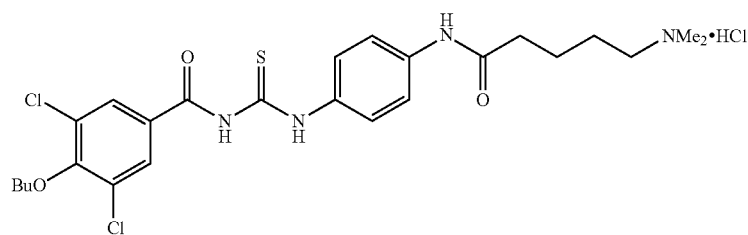

Synthesised according to general procedure A from 4-butoxy-3,5-dichloro-benzoyl chloride (prepared according to general procedure B from 4-butoxy-3,5-dichloro-benzoic acid). Purification by column chromatography eluting with methanol/dichloromethane (0% to 20%) followed by treatment with 2 M hydrochloric acid in diethyl ether gave 392a (5 mg) as a yellow oil. $^1$H NMR (MeOD, 400 MHz) δ 0.97 (t, 2H, J=7.4 Hz, $CH_3$), 1.57 (m, 2H, $CH_2$), 1.77 (m, 6H, $(CH_2)_3$), 2.46 (m, 2H, $CH_2$), 2.85 (s(br), 6H, $N(CH_3)_2$), 3.13 (m, 2H, $CH_2$), 4.07 (q, 2H, J=6.6 Hz, $CH_2$), 7.59 (apparent s, 4H, ArH), 7.96 (s, 2H, ArH). LRMS ES+ (M-Cl) Found 539.00.

3,5-Dichloro-4-ethoxy-benzoic acid 3,5-Dichloro-4-hydroxy-benzoic (400 mg, 1.93 mmol) was stirred in tetrahydrofuran (5 mL) with 40% aqueous n-tetrabutyl phosphonium hydroxide (3.16 mL, 3.86 mmol) at 0° C. for 5 mins and iodoethane (219 μL, 1.93 mmol) added. The reaction mixture was left to warm to room temperature and stirred for 6 h. The solution was concentrated in vacuo and the remaining residue acidified with concentrated hydrochloric acid to give a white suspension. The mixture was extracted with dichloromethane (3×25 mL) and the combined organic phases washed with saturated brine. The organic layer was dried ($MgSO_4$) and concentrated in vacuo to give a crude mixture which was purified by column chromatography eluting with methanol/dichloromethane (0% to 5%) to give 3,5-dichloro-4-ethoxy-benzoic acid (120 mg, 27%) as a white powder. $^1$H NMR ($CDCl_3$, 400 MHz) δ 1.47 (t, 3H, J=6.8 Hz, $CH_3$), 4.17 (q, 2H, J=7.1 Hz, $CH_2$).

5-Dimethylamino-pentanoic acid {4-[3-(3,5-dichloro-4-ethoxy-benzoyl)-thioureido]-phenyl}-amide hydrochloride (391a)

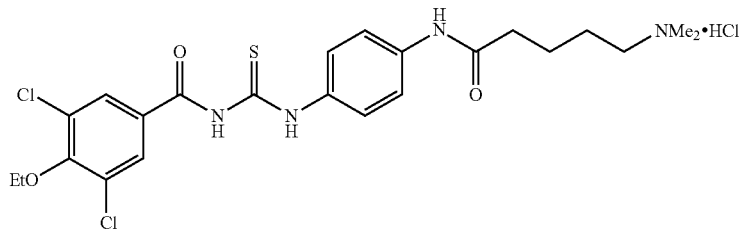

Synthesised according to general procedure A from 3,5-dichloro-4-ethoxy-benzoyl chloride (prepared according to general procedure B from 3,5-dichloro-4-ethoxy-benzoic acid). Purification by column chromatography eluting with methanol/dichloromethane (0% to 20%) followed by treatment with 2 M hydrochloric acid in diethyl ether gave AM391a (4 mg) as a yellow oil. $^1$H NMR (MeOD, 300 MHz), δ 1.45 (t, 3H, J=7.0 Hz, CH$_3$), 1.77 (m, 4H, (CH$_2$)$_2$), 2.45 (m, 2H, CH$_2$), 2.88 (s, 6H, N(CH$_3$)$_2$), 3.06 (m, 2H, CH$_2$), 4.18 (q, 2H, J=7.1 Hz, CH$_2$), 7.61 (m, 4H, ArH), 7.99 (s, 2H, ArH). LRMS ES+ (M-Cl) Found 510.99.

SIRT1 and SIRT2 Inhibition Assays

All compounds were tested for inhibition of SIRT1 and SIRT2 using human recombinant enzymes available in the Fluor de Lys fluorescence-based assay kit (BIOMOL, AK555, AK556). All other required reagents were provided in the kit which was stored at −78° C. Before use, small aliquots of each enzyme (2-3 μL) were prepared, snap frozen in liquid nitrogen and stored at −78° C. Fresh dilutions of compounds were prepared in DMSO and further diluted in assay buffer. NAD$^+$ (12.5 ΞL at 4 mM) and Fluor de Lys SIRT1 or SIRT2 (12.5 μL at 100 μM) in assay buffer were added to a white 96 well plate, followed by compound (10 μL) and lastly enzyme (15 μL, 0.07 U/μL or SIRT1 and 0.3 U/μL for SIRT2). After incubation for 1 h at 37° C. a developer solution (50 μL) was added to each reaction. The developer solution contained 38 μL buffer, 10 μL developer and 2 μL nicotinamide (50 mM) per reaction. The plate was then incubated for 45 min at rt and then read using a Spectra Max Gemini fluorimeter with an excitation wavelength of 355 nm and an emission wavelength of 460 nm. SigmaPlot software was used to generate fit curves for raw plots and the equation for each curve was used to calculate IC$_{50}$ data.

Inhibition of SIRT1 and SIRT2 by Tenovin-6 Analogues

| Compound Number (*) | SirT1 (% inhib at 60 μM) | SirT1 IC$_{50}$ (μM) | SirT2 (% inhib at 60 μM) | SirT2 IC$_{50}$ (μM) |
|---|---|---|---|---|
| 4-$^t$butyl ** | 71.7 | 21 | 93.1 | 10 |
| A1 (2-Me) | 10 | >90 | 48.5 | 80.7 ± 14.4 |
| A2 (2-Cl) | 29.3 | — | 54.3 | — |
| A3 (2-OMe) | 48.7 | — | 66.8 | — |
| A5 (3-Cl) | 29.2 | — | 57.9 | — |
| A6 (3-Br) | 70.5 | 39.9 ± 8.1 | 81 | 21.2 ± 7.2 |
| B1 (3-Me) ** | 5 | >90 | 20.9 | >90 |
| B2 (3-OMe) ** | 25.3 | — | 30.5 | — |
| B4 (4-H) ** | 3.5 | >90 | 43.7 | >90 |
| 318a A1 (4-Cl) | 53 | — | 61 | — |
| B5 (4-Br) | 13.5 | 62.1 ± 2.3 | 47.7 | 39.5 ± 9.7 |
| 318a A2 (4-Me) | 47 | — | 40 | — |
| 318a A3 (4-OMe) | 48 | — | 51 | — |
| B6 (4-CF$_3$) | 10.9 | — | 17.1 | — |
| 331a (4-isopropyl) | 52.9 | 64.8 ± 3.8 | 78.4 | 32.5 ± 0.07 |
| 332a (4-NMe$_2$) | 55.7 | — | 61.5 | — |
| C4 (3,4-Me$_2$) ** | 27.5 | — | 65.1 | — |
| 330a (3-Br, 4-Me) | 33 | 43.9 ± 7.3 | 80.2 | 31.9 ± 1.6 |
| C5 (3-Me, 4-Br) ** | 24 | 69.6 ± 0.6 | 77.1 | 34.3 ± 7.2 |
| C6 (3-CF$_3$, 4-OMe) ** | 58.3 | 51.7 ± 6.9 | 29.5 | >90 |
| 311d (3,4-Cl$_2$) | 8 | 70.9 ± 4.2 | 68 | 31.9 ± 6.4 |
| 350a (3-Cl, 4-OMe) | 9 | — | 37.8 | — |
| D1 (3,4,5-F$_3$) | 7.5 | >90 | 46 | 52.5 ± 12.3 |
| D2 (3,4,5-(OMe)$_3$) ** | 12.5 | — | 18 | — |
| D3 (3-Cl, 4-OMe, 5-Cl) | 35 | 62.5 ± 3.6 | 80.3 | 10.7 ± 1.6 |
| 345a (4-n-penyl) | 73 | — | 85.4 | — |
| 345b (4-n-butyl) | 56.3 | — | 90 | — |
| 345c (4-n-propyl) | 82.4 | — | 89 | — |
| 345d (4-ethyl) | 9.1 | — | 57.1 | — |
| 361a (3-Br, 4 $^t$Bu) | 93.5 | 18.3 ± 0.3 | 91.1 | 4.6 ± 0.6 |
| 360a (3,5-Cl$_2$) | 23.3 | — | 49.9 | — |
| 383a (3,5-Br$_2$, 4-OMe) | 66.2 | 47.2 ± 0.9 | 82.7 | 14 ± 1.7 |
| 392a (3,5-Cl$_2$, 4-OBu) | 90.4 | 22.5 ± 1.3 | 96.3 | 0.4 ± 0.4 |
| 391a (3,5-Cl$_2$, 4-OEt) | 81.5 | 29.3 ± 3.6 | 87.9 | 3 ± 0.1 |

(*) Substitution pattern in brackets indicates the position of substitution in the phenyl Ar' group of the compound:

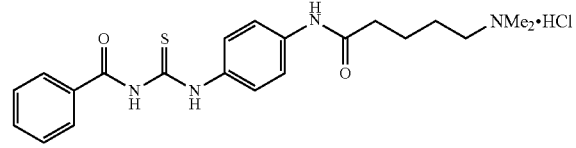

(**) Compounds indicates with double asterisk are not examples of the invention but inhibition date and experimental above are included to allow a better understanding of the invention.

Adipocyte Differentiation Assay

3T3L1 cells (i.e. mouse fibroblasts that differentiate into adipocytes in so-called differentiation medium) were treated in a low glucose differentiation medium (as described by F Wang and Q Tong (*Molecular Biology of the Cell*, 20, 2009, 801-808) with either (i) a normal growth medium (DMEM), (ii) a low glucose differentiation medium containing ciglitazone, d-biotin, dexamethasone, IBMX, insulin and L-thyroxine, or a (iii) a low glucose differentiation medium as per (ii) but lacking one of the components (i.e 6 different media each comprising five components selected from ciglitazone, d-biotin, dexamethasone, IBMX, insulin and L-thyroxine). Cells were stained with ORO red to detect lipid.

The same differentiation assays with each of the 8 differentiation media were then repeated but with addition of DMSO solvent and also 10 μM of compound D3 (5-dimethylamino-pentanoic acid {4-[3-(3,5-dichloro-4-methoxy-benzoyl)-thioureido]-phenyl}-amide hydrochloride) in duplicate.

Compound D3 generally increases the oro red staining, versus the controls, both with and without DMSO, showing enhanced adipogenesis in its presence.

The invention claimed is:

1. A compound according to formula (I):

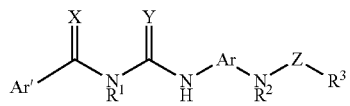

(I)

wherein:
X is O and Y is S;
—Z— is —C(O)—;
Ar is 1,4-phenylene;
each of —$R^1$ and —$R^2$ is —H, and —$R^3$ is an amino-substituted, saturated, straight chain C3-C10 alkyl group; and
Ar'— is a moiety of formula (II)

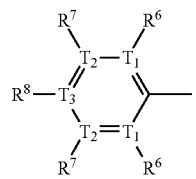

(II)

wherein:
each $T_1$, $T_2$, and $T_3$ is a carbon atom, where each $R^6$ is independently selected from the group consisting of hydrogen, $O_{1-6}$ alkyl, halo, $C_{1-6}$ alkoxy, alkylthio, alkylamino and dialkylamino;
each $R^7$ is independently selected from the group consisting of hydrogen, halo, nitro, cyano, carboxy, formyl or C(=O)$R^4$, C(=S)$R^4$, C(=O)$SR^4$, C(=S)$SR^4$, C(=O)$NH_2$ and C(=S)$NH_2$ wherein (i) one or both hydrogen atoms of C(=O)$NH_2$ and C(=S)$NH_2$ may be independently exchanged for $R^4$, C(O)$R^4$, S(O)$R^4$, S(O)$_2R^4$ and SO$_2OR^4$, and (ii) at least one $R^7$ is not hydrogen; and $R^8$ is selected from the group consisting of alkyl, alkoxy, alkylthio, OH, SH, halo, NHC(=O)$R^4$, NHC(=S)$R^4$ or $NH_2$ wherein one or both hydrogen atoms of the $NH_2$ may be independently exchanged for $R^4$, OC(=O)$R^4$, OC(=S)$R^4$, SC(=O)$R^4$, or SC(=S)$R^4$,
each $R^4$ is independently selected from the group consisting of alkyl and aryl,
or a physiologically acceptable salt or solvate thereof.

2. The compound of claim 1, or a physiologically acceptable salt or solvate thereof, wherein $R^8$ is a branched alkyl group.

3. The compound of claim 1, or a physiologically acceptable salt or solvate thereof, wherein $R^8$ is an alkyl group.

4. The compound of claim 1, or a physiologically acceptable salt or solvate thereof, wherein $R^8$ is selected from the group consisting of alkyl, alkoxy, and $NH_2$ wherein one or both hydrogen atoms of the $NH_2$ may be independently exchanged for alkyl.

5. The compound of claim 1, or a physiologically acceptable salt or solvate thereof, wherein both $R^6$s are hydrogen.

6. The compound of claim 1, or a physiologically acceptable salt or solvate thereof, wherein neither $R^7$ is hydrogen.

7. The compound of claim 6, or a physiologically acceptable salt or solvate thereof, wherein each $R^7$ is halo.

8. The compound of claim 1, or a physiologically acceptable salt or solvate thereof, wherein $R^3$ is substituted with one or more amino groups.

9. The compound of claim 8, or a physiologically acceptable salt or solvate thereof, wherein $R^3$ is substituted once at its end distal to Z.

10. The compound of claim 8, or a physiologically acceptable salt or solvate thereof, wherein the amino group is morpholino.

11. The compound of claim 8, or a physiologically acceptable salt or solvate thereof, wherein the amino group is quaternized.

12. A pharmaceutical composition comprising a compound as defined in claim 1, or a physiologically acceptable salt or solvate thereof, together with a pharmaceutically acceptable carrier.

13. The compound of claim 1, wherein the compound is 5-dimethylamino-pentanoic acid {4-[3-(4-butoxy-3,5-dichloro-benzoyl)-thioureido]-phenyl}-amide.

14. The compound of claim 1, wherein the compound is 5-dimethylamino-pentanoic acid {4-[3-(4-butoxy-3,5-dichloro-benzoyl)-thioureido]-phenyl}-amide hydrochloride.

* * * * *